(12) United States Patent
Köster et al.

(10) Patent No.: US 6,730,517 B1
(45) Date of Patent: May 4, 2004

(54) AUTOMATED PROCESS LINE

(75) Inventors: Hubert Köster, La Jolla, CA (US);
Ping Yip, San Diego, CA (US); Jhobe Steadman, San Diego, CA (US); Dirk Reuter, Hamburg (DE); Richard MacDonald, San Diego, CA (US)

(73) Assignee: Sequenom, Inc., San Diego, CA (US)

( * ) Notice: Subject to any disclaimer, the term of this patent is extended or adjusted under 35 U.S.C. 154(b) by 465 days.

(21) Appl. No.: 09/680,581

(22) Filed: Oct. 5, 2000

Related U.S. Application Data

(62) Division of application No. 09/285,481, filed on Apr. 2, 1999.

(51) Int. Cl.[7] ............ G01N 35/02; H05H 3/02; G05B 21/00
(52) U.S. Cl. ............ 436/47; 436/43; 436/173; 436/131; 422/63; 422/65; 422/67; 422/102; 250/251; 250/282; 250/287; 250/288; 700/266
(58) Field of Search ............ 422/63, 65, 67, 422/102; 436/43, 47, 173, 131; 250/251, 282, 287, 288; 700/266

(56) References Cited

U.S. PATENT DOCUMENTS

| | | | |
|---|---|---|---|
| 3,789,203 A | 1/1974 | Catherall et al. | 235/152 |
| 4,031,370 A | 6/1977 | Catherall | 235/152 |
| 4,076,982 A | 2/1978 | Ritter et al. | 250/288 |
| 4,490,806 A | 12/1984 | Enke et al. | 708/445 |
| 4,791,577 A | 12/1988 | Winter | 702/77 |
| 4,826,360 A | 5/1989 | Iwasawa et al. | 406/51 |
| 4,851,018 A | 7/1989 | Lazzari et al. | 55/356 |
| 5,121,337 A | 6/1992 | Brown | 364/498 |
| 5,122,342 A | 6/1992 | McCulloch et al. | 422/65 |
| 5,124,932 A | 6/1992 | Lodder | 702/30 |

(List continued on next page.)

FOREIGN PATENT DOCUMENTS

| | | |
|---|---|---|
| EP | 0296781 | 6/1988 |
| EP | 0299652 | 1/1989 |
| EP | 0395481 | 10/1990 |
| EP | 0596205 | 5/1994 |
| EP | 2749662 | 12/1997 |

(List continued on next page.)

OTHER PUBLICATIONS

Cai et al., "Different discrete wavelet transforms applied to denoising analytical data", *J. Chem. Inf. Comput. Sci.*, 38(6):1161–1170 (1998).

Li et al., "De–noising ENMR spectra by wavelet shrinkage," *Proceedings of the 11th IEEE Symposium on Computer–Based Medical Systems. CBMS '98*. Lubbock, TX, Jun. 12–14, 1998, IEEE Symposium on Computer–Based Medical Systems, Los Alamitos, CA: IEEE Computer Soc. US, Jun. 12, 1998. pp 252–255.

(List continued on next page.)

*Primary Examiner*—Jill Warden
*Assistant Examiner*—LaToya Cross
(74) *Attorney, Agent, or Firm*—Stephanie L. Seidman; Fish & Richardson P.C.

(57) ABSTRACT

Fully automated modular analytical systems with integrated instrumentation for analysis of biopolymer samples, such as nucleic acids, proteins, peptides and carbohydrates, are provided. Analytical methods of detection and analysis, such as mass spectrometry, radiolabeling, mass tags, chemical tags and fluorescence chemiluminescence, are integrated with robotic technology and automated chemical reaction systems to provide a high-throughput, accurate Automated Process Line (APL).

14 Claims, 7 Drawing Sheets

U.S. PATENT DOCUMENTS

| | | | |
|---|---|---|---|
| 5,175,430 A | 12/1992 | Enke et al. | 250/282 |
| 5,247,175 A | 9/1993 | Schoen et al. | 250/281 |
| 5,273,718 A | 12/1993 | Sköld et al. | 422/101 |
| 5,363,885 A | 11/1994 | McConnell et al. | 141/1 |
| 5,379,238 A | 1/1995 | Stark | 703/11 |
| 5,428,357 A | 6/1995 | Haab et al. | 341/155 |
| 5,440,119 A | 8/1995 | Labowsky | 250/282 |
| 5,453,613 A | 9/1995 | Gray et al. | 250/281 |
| 5,490,516 A | 2/1996 | Hutson | 600/508 |
| 5,498,545 A | 3/1996 | Vestal | 436/47 |
| 5,547,835 A | 8/1996 | Köster | 435/6 |
| 5,592,402 A | 1/1997 | Beebe et al. | 703/6 |
| 5,605,798 A | 2/1997 | Köster | 435/6 |
| 5,622,824 A | 4/1997 | Köster | 435/6 |
| 5,635,713 A | 6/1997 | Labowsky | 250/282 |
| 5,686,656 A | 11/1997 | Amirav et al. | 73/23.41 |
| 5,691,141 A | 11/1997 | Köster | 435/6 |
| 5,851,765 A | 12/1998 | Köster | 435/6 |
| 5,853,979 A | 12/1998 | Green et al. | 435/5 |
| 5,869,242 A | 2/1999 | Kamb | 435/6 |
| 5,872,003 A | 2/1999 | Köster | 435/283.1 |
| 5,885,841 A | 3/1999 | Higgs, Jr. et al. | 436/89 |
| 5,900,481 A | 5/1999 | Lough et al. | 536/55.3 |
| 5,928,906 A | 7/1999 | Köster et al. | 435/91.2 |
| 5,928,952 A | 7/1999 | Hutchins et al. | 436/50 |
| 5,975,492 A | 11/1999 | Brenes | 251/175 |
| 5,985,214 A | 11/1999 | Stylli et al. | 422/65 |
| 5,995,989 A | 11/1999 | Gedcke et al. | 708/300 |
| 6,017,693 A | 1/2000 | Yates, III et al. | 435/5 |
| 6,022,688 A | 2/2000 | Jurinke et al. | 435/6 |
| 6,024,925 A | 2/2000 | Little et al. | 422/100 |
| 6,043,031 A | 3/2000 | Köster et al. | 435/6 |
| 6,060,022 A | 5/2000 | Pang et al. | 422/65 |
| 6,094,050 A | 7/2000 | Zaroubi et al. | 324/309 |
| 6,111,251 A | 8/2000 | Hillenkamp | 250/288 |
| 6,132,685 A | 10/2000 | Kercso et al. | 422/104 |
| 6,133,436 A | 10/2000 | Köster et al. | 536/24.3 |
| 6,140,053 A | 10/2000 | Köster | 435/6 |
| 6,146,854 A | 11/2000 | Köster et al. | 435/1.1 |
| 6,147,344 A | 11/2000 | Annis et al. | 250/281 |
| 6,188,064 B1 | 2/2001 | Koster | 250/282 |
| 6,270,835 B1 | 8/2001 | Hunt et al. | 427/79 |
| 2002/0009394 A1 | 1/2002 | Koster et al. | 422/65 |

FOREIGN PATENT DOCUMENTS

| | | |
|---|---|---|
| GB | 2329475 | 3/1999 |
| WO | 9315407 | 8/1993 |
| WO | 9321592 | 10/1993 |
| WO | 9416101 | 7/1994 |
| WO | 9421822 | 9/1994 |
| WO | 9629431 | 9/1996 |
| WO | 9708306 | 3/1997 |
| WO | 9737041 | 10/1997 |
| WO | 9742348 | 11/1997 |
| WO | 9743617 | 11/1997 |
| WO | 9812734 | 3/1998 |
| WO | 9820019 | 5/1998 |
| WO | 9820020 | 5/1998 |
| WO | 9820166 | 5/1998 |
| WO | 9833808 | 8/1998 |
| WO | 9912040 | 3/1999 |
| WO | 9931278 | 6/1999 |
| WO | 9957318 | 11/1999 |
| WO | 0056446 | 9/2000 |
| WO | 0060361 | 10/2000 |
| WO | 0127857 | 4/2001 |

OTHER PUBLICATIONS

Norris et al., "Real–time compression of myoelectric data utilising adaptive differential pulse code modulation", *Med. Biol. Eng. Comput.*, Peter Peregrinus LTD.Stevenage, GB. 33(5): 629–635 (1995).

Nelson, S.J. and T.R. Brown, "Accuracy of Quantification from 1D NMR Spectra Using the PIQABLE Algorithm," *Journal of Magnetic Resonance* 84:95–109 (1989).

Polettini et al. "Fully–automated systematic toxicological analysis of drugs, poisons, and metabolites in whole blood, urine, and plasma by gas chromatography–full scan mass spectrometry," *Journal of Chromatography B* 713:265–279 (1998).

Badger et al., New features and enhancements in the X–PLOR computer program, *Proteins* 35(1):25–33 (1999).

Braun et al., Improved analysis of microsatellites using mass spectrometry, *Genomics* 46(10:18–23 (1997).

Database WPI, Derwent publication # 011635345 citing International Patent Application WO 9747974 of the parent French Patent Application FR 2,749,662.

Goldmacher et al., Photoactivation of toxin conjugates, *Bioconj. Chem.* 3:104–107 (1992).

Hazum et al., A photocleavable protecting group for the thiol function of cysteine, in *Pept., Proc. Eur. Pept. Symp.*, 16th Brunfeldt, K (ed), pp. 105–110– (1981).

Hinton et al., "The application of robotics to fluorometric and isotopic analyses of uranium.", Laboratory Automation & Information Management, NL, Elsevier Science publishers BV., Amsterdam, vol. 21 No. 2/03, pp. 223–227, Dec. 1, 1993.

Instrumentation; Bar code systems, including one and two dimensional bar codes, readable and readable/writable codes and systems; Datalogic S.p.A. of Italy ("Datalogic") located at http://www.datalogic.com.

Instrumentation; DYNABEADS, streptavidin–coated magnetic beads; from Dynal, Inc. Great Neck, NY and Oslo Norway.

Instrumentation; "MJ Microseal" plate sealer; Thermal Cycler Accessories: Sealing Options, Sealing Products, MJ Research, located at http://www.mjresearch.com/html/consumables/ealing/sealing_products.html.

Instrumentation; "Multimek 96" automated pipettor; Beckman Coulter, Inc. located at http://www.coulter.com, Sep. 8, 1999.

Instrumentation; "Model CRS A 255" robot "Digital Servo Gripper" "Plate Cube" system. "lid parking station" "shaker" Robocon Labor–und Industrieroboter Ges.m.b.H of Austria ("Robocon").

Instrumentation; "Nano–Plotter" from GeSiM, Germany, located at http:/www.gesim.de/np–intro.htm.

Instrumentation; "Genesis 200/8" (200 cm with including an 8–tip arm) liquid handling systems; Tecan AG of Switzerland ("Tecan"), TECAN Products for Diagnostics and Life Science, located at http://www.tecan.ch/index.htm.

International Search Report for International Application No. PCT/US00/08111, Date of Mailing Nov. 11, 2000.

Little et al., MALDI on a chip: analysis of arrays of low–femtomole to subfemtomole quantities of synthetic oligonucleotides and DNA diagnostic products dispensed by a piezoelectric pipet, *Anal. Chem.* 69:4540–4546 (1997).

Little et al., Identification of apolipoprotein E polymorphisms using temperature cycled primer oligo base extension and mass spectrometry, *Eur J clin Chem Clin Biochem* 35(7):545–8 (1997).

Nilges et al., Automated NOESY interpretation with ambiguous distance restraints: the refined NMR solution structure of the pleckstrin homology domain from β–spectrin, *J. Mol. Biol.* 269:408–422 (1997).

Senko et al., Automated Assignment of Charge States from Resolved Isotopic Peaks for Multiply Charged Ions, *J. Am. Soc. Mass Spectrom* 6:52–56 (1995).

Senter et al., Novel photocleavable protein crosslinking reagents and their use in the preparation of antibody–toxin conjugates, *Photochem. Photobiol.* 42:231–237 (1985).

Sequenom Advances the Industrial Genomics Revolution with the Launch of Its DNA MassArray™ Automated Process Line, Press Release: Sep. 28, 1998, http://www.sequenom.com/pressrelease.htm.

Sequenom: Technologies and Tools, located at http://www.sequenom-san.com/tech/tools.html, dated Aug. 29, 1999.

Tammen et al., Proteolytic cleavage of glucagon–like peptide–1 by pancreatic β cells and by fetal calf serum analyzed by mass spectrometry, *J. Cromatogr. A* 852:285–295 (1999).

Thompson, Fitting robots with white coats, *Laboratory Automation and Information Management* 31:173–193 (1996).

Wang et al., Allene $\gamma_9$ and $\gamma_{10}$: low–temperature measurements of line intensity, *J Mol Spectrosc* 194(20:256–268 (1999).

Weiler et al., Hybridisation based DNA screening on peptide nucleic acid (PNA) oligomer arrays, *Nucleic Acids Res.* 25:2792–2799 (1997).

Yen et al., Synthesis of water–soluble copolymers containing photocleavable bonds, *Makromol. Chem.* 190:69–82 (1989).

Bessant et al., "Integrated processing of triply coupled diode array liquid chromatography electrospray mass spectrometric signals by chemometric methods", *Analysis*, 124:1733–1744 (1999).

Bluck et al., "Peak Measurement in Gas Chromatographic/Mass Spectrometric Isotope Studies", *J. Mass Spectrometry*, 32:1212–1218 (1997).

Hindmarch, et al. "Deconvolution and Spectral Clean–up of Two–component Mixtures by Factor Analysis of Gas Chromatographic–Mass Spectrometric Data", *Analyst(Aug.)*, 121:993–1001 (1996).

Sehgal et al. Isolation and Characterization of a novel gene from human gliobalstoma multiform tumor tissue. International Journal of Cancer. 1997. vol. 71, pp. 565–572.

FIG. 7

| From here you can: | | Automatic Process Line Database analysis system | |
|---|---|---|---|
| Go | Create a new Run | | |
| Go | Copy an existing Run | | You can copy a Run in order to re-run it on the APL |
| Go | Edit/View an existing Run | AMG1 ▶ | You can edit a Run or view the results |
| Go | Change status/Add comment | AMG1 ▶ | Change the status from Setup to Running to Finished |
| Go | View the history of a Run | AMG1 ▶ | |
| Go | Create/Edit an Assay/Test | New ▶ | Create each Test before creating any Runs that use that Test. |

[Home][Download][Runs][Assays]

| Previous100 | Next100 | StartAt | 100 | Find | | Select ☐ |

AMGI Results

| Row | Reaction_Details | | | | Sample_Details | | | | Assay_Details | | | |
|---|---|---|---|---|---|---|---|---|---|---|---|---|
| | PlateNo. | PlateID | Well | SampleNo. | SampleID | PlateNo. | PlateID | Well | AssayNo. | Name | Result | Spectrum |
| 1 | 1 | 11S7872 | A1 | 1 | 14G88 | 1 | 23R902 | A1 | 1 | AMG | MALE | 11S7872_A1.sq |
| 2 | 1 | 11S7872 | A2 | 2 | 14G89 | 1 | 23R902 | A2 | 1 | AMG | MALE | 11S7872_A2.sq |
| 3 | 1 | 11S7872 | A3 | 3 | 14G90 | 1 | 23R902 | A3 | 1 | AMG | FEMALE | 11S7872_A3.sq |
| 4 | 1 | 11S7872 | A4 | 4 | 14G91 | 1 | 23R902 | A4 | 1 | AMG | FEMALE | 11S7872_A4.sq |
| 5 | 1 | 11S7872 | A5 | 5 | 14G92 | 1 | 23R902 | A5 | 1 | AMG | MALE | 11S7872_A5.sq |
| 6 | 1 | 11S7872 | A6 | 6 | 14G93 | 1 | 23R902 | A6 | 1 | AMG | FEMALE | 11S7872_A6.sq |
| 7 | 1 | 11S7872 | A7 | 7 | 14G94 | 1 | 23R902 | A7 | 1 | AMG | MALE | 11S7872_A7.sq |
| 8 | 1 | 11S7872 | A8 | 8 | 14G95 | 1 | 23R902 | A8 | 1 | AMG | FEMALE | 11S7872_A8.sq |
| 9 | 1 | 11S7872 | A9 | 9 | 14G96 | 1 | 23R902 | A9 | 1 | AMG | MALE | 11S7872_A9.sq |
| 10 | 1 | 11S7872 | A10 | 10 | 14G97 | 1 | 23R902 | A10 | 1 | AMG | MALE | 11S7872_A10.sq |
| 11 | 1 | 11S7872 | A11 | 11 | 14G98 | 1 | 23R902 | A11 | 1 | AMG | FEMALE | 11S7872_A11.sq |
| 12 | 1 | 11S7872 | A12 | 12 | 14G99 | 1 | 23R902 | A12 | 1 | AMG | FEMALE | 11S7872_A12.sq |
| 13 | 1 | 11S7872 | B1 | 13 | 14G100 | 1 | 23R902 | B1 | 1 | AMG | MALE | 11S7872_B1.sq |
| 14 | 1 | 11S7872 | B2 | 14 | 14G101 | 1 | 23R902 | B2 | 1 | AMG | FEMALE | 11S7872_B2.sq |
| 15 | 1 | 11S7872 | B3 | 15 | 14G102 | 1 | 23R902 | B3 | 1 | AMG | MALE | 11S7872_B3.sq |
| 16 | 1 | 11S7872 | B4 | 16 | 14G103 | 1 | 23R902 | B4 | 1 | AMG | FEMALE | 11S7872_B4.sq |
| 17 | 1 | 11S7872 | B5 | 17 | 14G104 | 1 | 23R902 | B5 | 1 | AMG | MALE | 11S7872_B5.sq |

FIG. 8

AUTOMATED PROCESS LINE

RELATED APPLICATIONS

This application is a divisional of U.S. application Ser. No. 09/285,481 to Hubert Köster, Ping Yip, Jhobe Steadman, Dirk Reuter and Richard MacDonald, filed Apr. 2, 1999, entitled "AUTOMATED PROCESS LINE" is claimed. U.S. application Ser. No. 09/285,481 is incorporated by reference in its entirety.

BACKGROUND OF THE INVENTION

In recent years, developments in the field of life sciences have proceeded at a breathtaking rate. Ground breaking scientific discoveries and advances in such fields as genomics (sequencing and characterization of genetic information and analysis of the relationship between gene activity and cell function) and proteomics (systematic analysis of protein expression in tissues, cells, and biological systems) promise to reshape the fields of medicine, agriculture, and environmental science. The success of these efforts depends, in part, on the development of sophisticated laboratory tools that will automate and expedite the testing and analysis of biological samples.

Current methods of testing typically employ multiple instruments for preparing and analyzing samples and involve multiple manual handling steps and transfers. Such procedures are labor-intensive, time-consuming, and costly and they are susceptible to human error, sample contamination, and loss. After samples have been prepared, they can be subjected to testing procedures that produce data for analysis. Conventional testing procedures often must be performed by an individual laboratory technician, one sample at a time. Laboratory technicians are typically individuals who are most likely trained to operate only a single instrument. Automation will reduce the number of personnel and training necessary to carry out the research. Reliable and accurate automated process and analysis tools are necessary for the benefits of recent scientific discoveries to be fully achieved.

Genomic research is increasing the availability of genomic markers that can be used for the identification of all organisms, including humans. These markers (all genetic loci including SNPs, microsatellites and other noncoding genomic regions) provide a way to not only identify populations but also allow stratification of populations according to their response to drug treatment, resistance to environmental agents, and other factors. Importantly, the identification of the large number of genomic markers has become the driving force behind the development of new automated technologies.

At the forefront of the efforts to develop better analytical tools are efforts to expedite the analysis of complex biochemical structures. For example, robotic devices have been employed to assist in sample preparation and handling.

Such automated sample preparation systems could find application is the areas of: identification and validation of disease-causing genes or drug targets; defining mutations and polymorphisms associated with specific diseases; monitoring gene expression and comparing disease states, cell cycles or other changes; genetic profiling of patients for responsiveness to genomics-based therapies; and genetic profiling of subjects in drug clinical studies to link response with genotype.

The utility of genomic markers to identify and stratify populations is depending on the industry's ability to measure great numbers (100–100,000) of markers in large populations. This approach is extremely limited in terms of time and research costs. Automation of these systems provides advantages such as increasing throughput and accuracy, but miniaturization also is an important consideration in terms of research costs. Accordingly, there is a need to automate processes in which very small volumes are handled, and retain the accuracy of the results to permit their use in high throughput screening protocols and diagnostics.

Therefore it is an object herein to provide automated systems and methods for high-throughput analysis of biological samples, particularly samples of very small volume, for screening, diagnosis and other procedures. Other objects will become apparent from the following disclosure.

SUMMARY OF THE INVENTION

Provided herein is a fully automated modular analytical system that integrates sample preparation, instrumentation, and analysis of biopolymer samples. The samples include, but are not limited to, all biopolymers, e.g., nucleic acids, proteins, peptides, carbohydrates, PNA (peptide nucleic acids), biopolymer (nucleic acid/peptide) analogs, and libraries of combinatorial molecules. The system integrates analytical methods of detection and analysis including but are not limited to, mass spectrometry, radiolabeling, mass tags, chemical tags, fluorescence chemiluminescence, with robotic technology and automated chemical reaction systems to provide a high-throughput, accurate automated process line (APL). The systems and methods provided herein are particularly suited for handling very small volumes, on the order of milliliters, nanoliters and even smaller picoliter volumes.

In certain embodiments, the analytical system includes one portion that is a contamination-controlled environment, such as a clean room or laminar flow room, and includes a means, such as a transporter, for moving the samples from such environment into a second room or space for further processing. This dual space system permits performance of procedures that require clean room conditions to be automatedly linked to procedures that do not require such conditions.

An integrated system for performing a process line comprising a plurality of processing stations, each of which performs a procedure on a biological sample contained in a reaction vessel; a robotic system that transports the reaction vessel from processing station to processing station; a control system that determines when the procedure at each processing station is complete and, in response, moves the reaction vessel to the next test station, and continuously processes reaction vessels one after another until the control system receives a stop instruction; and a data analysis system that receives test results of the process line and automatically processes the test results to make a determination regarding the biological sample in the reaction vessel is provided.

The APL can run unattended continuously with a continuous sample throughput and is capable of analyzing on the order of 10,000–50,000 genotypes per day. The results are highly accurate and reproducible.

Also provided herein are methods for automated analysis of biopolymers using the integrated APL system. In preferred embodiments, provided are automated methods for preparing a biological sample for analysis; introducing the sample into an analytical instrument; recording sample data; automatically processing and interpreting the data; and storing the data in a bioinformatics database. In a particular embodiment, patient DNA samples are automatically analyzed to determine genotype.

BRIEF DESCRIPTION OF THE DRAWINGS

FIG. 7 shows an example of the user interface to the APL system.

FIG. 8 shows an example of the interface to a database of experimental mass spectral data.

DETAILED DESCRIPTION AND PREFERRED EMBODIMENTS

Definitions

Figure 1:
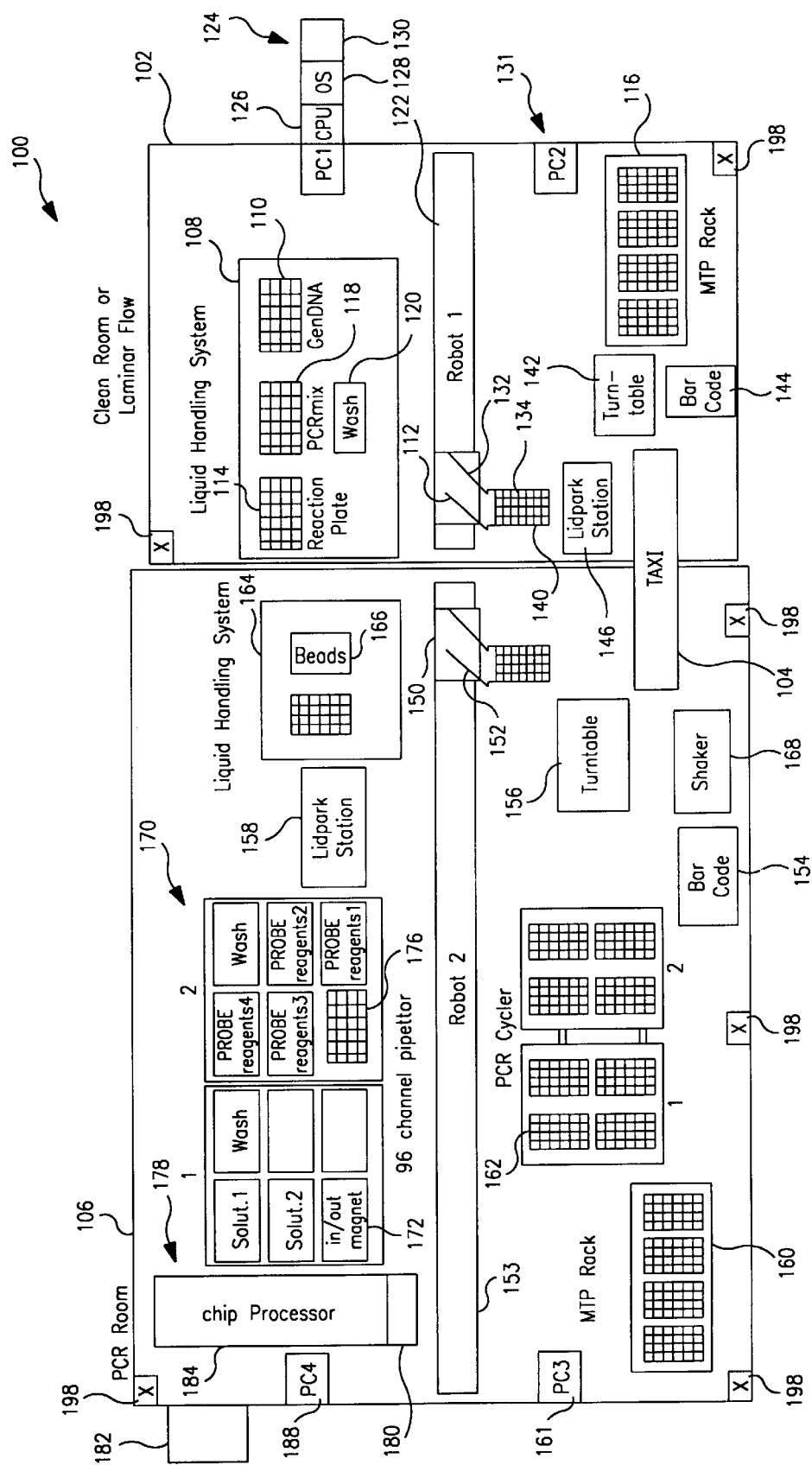
FIG. 1 is a diagram of the components of the automated process line.

Unless defined otherwise, all technical and scientific terms used herein have the same meaning as is commonly understood by one of skill in the art to which this invention belongs. All patents, patent applications and publications referred to herein are, unless noted otherwise, incorporated by reference in their entirety. In the event a definition in this section is not consistent with definitions elsewhere, the definition set forth in this section will control.

As used herein, a molecule refers to any molecule or compound that is linked to the bead. Typically such molecules are macromolecules or components or precursors thereof, such as peptides, proteins, small organics, oligonucleotides or monomeric units of the peptides, organics, nucleic acids and other macromolecules. A monomeric unit refers to one of the constituents from which the resulting compound is built. Thus, monomeric units include, nucleotides, amino acids, and pharmacophores from which small organic molecules are synthesized.

As used herein, macromolecule refers to any molecule having a molecular weight from the hundreds up to the millions. Macromolecules include peptides, proteins, nucleotides, nucleic acids, and other such molecules that are generally synthesized by biological organisms, but can be prepared synthetically or using recombinant molecular biology methods.

As used herein, a biological particle refers to a virus, such as a viral vector or viral capsid with or without packaged nucleic acid, phage, including a phage vector or phage capsid, with or without encapsulated nucleotide acid, a single cell, including eukaryotic and prokaryotic cells or fragments thereof, a liposome or micellar agent or other packaging particle, and other such biological materials. For purposes herein, biological particles include molecules that are not typically considered macromolecules because they are not generally synthesized, but are derived from cells and viruses.

As used herein, the term "nucleic acid" refers to single-stranded and/or double-stranded polynucleotides such as deoxyribonucleic acid (DNA), and ribonucleic acid (RNA) as well as analogs or derivatives of either RNA or DNA. Also included in the term "nucleic acid" are analogs of nucleic acids such as peptide nucleic acid (PNA), phosphorothioate DNA, and other such analogs and derivatives.

As used herein, the term "biological sample" refers to any material obtained from any living source (e.g., human, animal, plant, bacteria, fungi, protist, virus). For purposes herein, the biological sample will typically contain a nucleic acid molecule. Examples of appropriate biological samples include, but are not limited to: solid materials (e.g., tissue, cell pellets, biopsies) and biological fluids (e.g., urine, blood, saliva, amniotic fluid, mouth wash, cerebral spinal fluid and other body fluids).

As used herein, the phrases "chain-elongating nucleotides" and "chain-terminating nucleotides" are used in accordance with their art recognized meaning. For example, for DNA, chain-elongating nucleotides include 2'deoxyribonucleotides (e.g., dATP, dCTP, dGTP and dTTP) and chain-terminating nucleotides include 2',3'-dideoxyribonucleotides (e.g., ddATP, ddCTP, ddGTP, ddTTP). For RNA, chain-elongating nucleotides include ribonucleotides (e.g., ATP, CTP, GTP and UTP) and chain-terminating nucleotides include 3'-deoxyribonucleotides (e.g., 3'dA, 3'dC, 3'dG and 3'dU). A complete set of chain elongating nucleotides refers to dATP, dCTP, dGTP and dTTP. The term "nucleotide" is also well known in the art.

As used herein, nucleotides include nucleoside mono-, di-, and triphosphates. Nucleotides also include modified nucleotides such as phosphorothioate nucleotides and deazapurine nucleotides. A complete set of chain-elongating nucleotides refers to four different nucleotides that can hybridize to each of the four different bases comprising the DNA template.

As used herein, "multiplexing" refers to the simultaneously detection of more than one analyte, such as more than one (mutated) loci on a particular captured nucleic acid fragment (on one spot of an array).

As used herein, the term "biopolymer" is used to mean a biological molecule composed of two or more monomeric subunits, or derivatives thereof, which are linked by a bond or a macromolecule. A biopolymer can be, for example, a polynucleotide, a polypeptide, a carbohydrate, or a lipid, or derivatives or combinations thereof, for example, a nucleic acid molecule containing a peptide nucleic acid portion or a glycoprotein, respectively. The methods and systems herein, though described with reference to biopolymers, can be adapted for use with other synthetic schemes and assays, such as organic syntheses of pharmaceuticals, or inorganics and any other reaction or assay performed on a solid support or in a well in nanoliter volumes.

As used herein, the term "nucleic acid" refers to single-stranded and/or double-stranded polynucleotides such as deoxyribonucleic acid (DNA), and ribonucleic acid (RNA) as well as analogs or derivatives of either RNA or DNA. Also included in the term "nucleic acid" are analogs of nucleic acids such as peptide nucleic acid (PNA), phosphorothioate DNA, and other such analogs and derivatives.

As used herein, the term "polynucleotide" refers to an oligomer or polymer containing at least two linked nucleotides or nucleotide derivatives, including a deoxyribonucleic acid (DNA), a ribonucleic acid (RNA), and a DNA or RNA derivative containing, for example, a nucleotide analog or a "backbone" bond other than a phosphodiester bond, for example, a phosphotriester bond, a phosphoramidate bond, a phosphorothioate bond, a thioester bond, or a peptide bond (peptide nucleic acid). The term "oligonucleotide" also is used herein essentially synonymously with "polynucleotide," although those in the art will recognize that oligonucleotides, for example, PCR primers, generally are less than about fifty to one hundred nucleotides in length.

Nucleotide analogs contained in a polynucleotide can be, for example, mass modified nucleotides, which allows for mass differentiation of polynucleotides; nucleotides containing a detectable label such as a fluorescent, radioactive, luminescent or chemiluminescent label, which allows for detection of a polynucleotide; or nucleotides containing a reactive group such as biotin or a thiol group, which facilitates immobilization of a polynucleotide to a solid support. A polynucleotide also can contain one or more backbone bonds that are selectively cleavable, for example, chemically, enzymatically or photolytically. For example, a polynucleotide can include one or more deoxyribonucleotides, followed by one or more ribonucleotides, which can be followed by one or more deoxyribonucleotides, such a sequence being cleavable at the ribonucleotide sequence by base hydrolysis. A polynucleotide also can contain one or more bonds that are relatively resistant to cleavage, for example, a chimeric oligonucleotide primer, which can include nucleotides linked by peptide nucleic acid bonds and at least one nucleotide at the 3' end, which is linked by a phosphodiester bond, or the like, and is capable of being extended by a polymerase. Peptide nucleic acid sequences can be prepared using well known methods (see, for example, Weiler et al., *Nucleic acids Res.* 25:2792–2799 (1997)).

A polynucleotide can be a portion of a larger nucleic acid molecule, for example, a portion of a gene, which can contain a polymorphic region, or a portion of an extragenic region of a chromosome, for example, a portion of a region of nucleotide repeats such as a short tandem repeat (STR) locus, a variable number of tandem repeats (VNTR) locus, a microsatellite locus or a minisatellite locus. A polynucleotide also can be single stranded or double stranded, including, for example, a DNA-RNA hybrid, or can be triple stranded or four stranded. Where the polynucleotide is double stranded DNA, it can be in an A, B, L or Z configuration, and a single polynucleotide can contain combinations of such configurations.

As used herein, the term "polypeptide," means at least two amino acids, or amino acid derivatives, including mass modified amino acids and amino acid analogs, that are linked by a peptide bond, which can be a modified peptide bond. A polypeptide can be translated from a polynucleotide, which can include at least a portion of a coding sequence, or a portion of a nucleotide sequence that is not naturally translated due, for example, to it being located in a reading frame other than a coding frame, or it being an intron sequence, a 3' or 5' untranslated sequence, a regulatory sequence such as a promoter, or the like. A polypeptide also can be chemically synthesized and can be modified by chemical or enzymatic methods following translation or chemical synthesis. The terms "polypeptide,""peptide" and "protein" are used essentially synonymously herein, although the skilled artisan will recognize that peptides generally contain fewer than about fifty to one hundred amino acid residues, and that proteins often are obtained from a natural source and can contain, for example, post-translational modifications. A polypeptide can be post-translationally modified, such as by phosphorylation (phosphoproteins) and glycosylation (glycoproteins, proteoglycans), in a cell or in a reaction in vitro.

As used herein, the term "conjugated" refers stable attachment, preferably ionic or covalent attachment. Among preferred conjugation means are: streptavidin- or avidin- to biotin interaction; hydrophobic interaction; magnetic interaction (e.g., using functionalized magnetic beads, such as DYNABEADS, which are streptavidin-coated magnetic beads sold by Dynal, Inc. Great Neck, N.Y. and Oslo Norway); polar interactions, such as "wetting" associations between two polar surfaces or between oligo/polyethylene glycol; formation of a covalent bond, such as an amide bond, disulfide bond, thioether bond, or via crosslinking agents; and via an acid-labile or photocleavable linker.

As used herein equivalent, when referring to two sequences of nucleic acids means that the two sequences in question encode the same sequence of amino acids or equivalent proteins. When "equivalent" is used in referring to two proteins or peptides, it means that the two proteins or peptides have substantially the same amino acid sequence with only conservative amino acid substitutions that do not substantially alter the activity or function of the protein or peptide. When "equivalent" refers to a property, the property does not need to be present to the same extent [e.g., two peptides can exhibit different rates of the same type of enzymatic activity], but the activities are preferably substantially the same. "Complementary," when referring to two nucleotide sequences, means that the two sequences of nucleotides are capable of hybridizing, preferably with less than 25%, more preferably with less than 15%, even more preferably with less than 5%, most preferably with no mismatches between opposed nucleotides. Preferably the two molecules will hybridize under conditions of high stringency.

As used herein: stringency of hybridization in determining percentage mismatch are those conditions understood by those of skill in the art and typically are substantially equivalent to the following:

1) high stringency: 0.1×SSPE, 0.1% SDS, 65° C.

2) medium stringency: 0.2×SSPE, 0.1% SDS, 50° C.

3) low stringency: 1.0×SSPE, 0.1% SDS, 50° C.

It is understood that equivalent stringencies may be achieved using alternative buffers, salts and temperatures.

As used herein, a primer when set forth in the claims refers to a primer suitable for mass spectrometric methods requiring immobilizing, hybridizing, strand displacement, sequencing mass spectrometry refers to a nucleic acid must be of low enough mass, typically about 70 nucleotides or less than 70, and of sufficient size to be useful in the mass spectrometric methods described herein that rely on mass spectrometric detection. These methods include primers for detection and sequencing of nucleic acids, which require a sufficient number nucleotides to from a stable duplex, typically about 6–30, preferably about 10–25, more preferably about 12–20. Thus, for purposes herein a primer will be a sequence of nucleotides comprising about 6–70, more preferably a 12–70, more preferably greater than about 14 to an upper limit of 70, depending upon sequence and application of the primer. The primers herein, for example for mutational analyses, are selected to be upstream of loci useful for diagnosis such that when performing using sequencing up to or through the site of interest, the resulting fragment is of a mass that sufficient and not too large to be detected by mass spectrometry. For mass spectrometric methods, mass tags or modifier are preferably included at the 5'-end, and the primer is otherwise unlabeled.

As used herein, "conditioning" of a nucleic acid refers to modification of the phosphodiester backbone of the nucleic acid molecule (e.g., cation exchange) for the purpose of eliminating peak broadening due to a heterogeneity in the cations bound per nucleotide unit. Contacting a nucleic acid molecule with an alkylating agent such as akyliodide, iodoacetamide, β-iodoethanol, or 2,3-epoxy-1-propanol, the monothio phosphodiester bonds of a nucleic acid molecule can be transformed into a phosphotriester bond. Likewise, phosphodiester bonds may be transformed to uncharged derivatives employing trialkylsilyl chlorides. Further conditioning involves incorporating nucleotides that reduce sensitivity for depurination (fragmentation during MS) e.g., a purine analog such as N7- or N9-deazapurine nucleotides, or RNA building blocks or using oligonucleotide triesters or incorporating phosphorothioate functions that are alkylated or employing oligonucleotide mimetics such as peptide nucleic acid (PNA).

As used herein, the term "solid support" means a non-gaseous, non-liquid material having a surface. Thus, a solid support can be a flat surface constructed, for example, of glass, silicon, metal, plastic or a composite; or can be in the form of a bead such as a silica gel, a controlled pore glass, a magnetic or cellulose bead; or can be a pin, including an array of pins suitable for combinatorial synthesis or analysis.

As used herein, substrate refers to an insoluble support onto which a sample is deposited according to the materials described herein. Examples of appropriate substrates include beads (e.g., silica gel, controlled pore glass, magnetic, agarose gel and crosslinked dextrose (i.e. Sepharose and Sephadex, cellulose and other materials known by those of skill in the art to serve as solid support matrices. For examples substrates may be formed from any or combinations of: silica gel, glass, magnet, polystyrene/1% divinyl-benzene resins, such as Wang resins, which are Fmoc-amino acid-4-(hydroxymethyl)phenoxy-methylcopoly(styrene-1% divinylbenzene (DVD)) resin, chlorotrityl (2-chlorotritylchloride copolystyrene-DVB resin) resin, Merrifield (chloromethylated copolystyrene-DVB) resin metal, plastic, cellulose, cross-linked dextrans, such as those sold under the trade name Sephadex (Pharmacia) and agarose gel, such as gels sold under the trade name Sepharose (Pharmacia), which is a hydrogen bonded polysaccharide-type agarose gel, and other such resins and solid phase supports known to those of skill in the art. The support matrices may be in any shape or form, including, but not limited to: capillaries, flat supports such as glass fiber filters, glass surfaces, metal surfaces (steel, gold, silver, aluminum, copper and silicon), plastic materials including multiwell plates or membranes (e.g., of polyethylene, polypropylene, polyamide, polyvinylidenedifluoride), pins (e.g., arrays of pins suitable for combinatorial synthesis or analysis or beads in pits of flat surfaces such as wafers (e.g., silicon wafers) with or without plates, and beads. The supports include any supports used for retaining or conjugating macromolecules and biopolymers, and biological particles.

As used herein, a selectively cleavable linker is a linker that is cleaved under selected conditions, such as a photocleavable linker, a chemically cleavable linker and an enzymatically cleavable linker (i.e., a restriction endonuclease site or a ribonucleotide/RNase digestion). The linker is interposed between the support and immobilized DNA.

As used herein, the term "liquid dispensing system" means a device that can transfer a predetermined amount of liquid to a target site. The amount of liquid dispensed and the rate at which the liquid dispensing system dispenses the liquid to a target site, which can contain a reaction mixture, can be adjusted manually or automatically, thereby allowing a predetermined volume of the liquid to be maintained at the target site.

As used herein, the term "liquid" is used broadly to mean a non-solid, non-gaseous material, which can be homogeneous or heterogeneous and can contain one or more solid or gaseous materials dissolved or suspended therein. In general, a liquid is a component of a reaction mixture that is susceptible to evaporation under the conditions of the reaction. In particular, the liquid can be a solvent, in which a reaction is performed, for example water or glycerol/water or buffer or reaction mixture, where the reaction is performed in an aqueous solution. The liquid can be any non-solid, non-gaseous solvent or other component of a reaction mixture that is susceptible to evaporative loss, for example, acetonitrile, which can be a solvent for a nucleic acid synthesis reaction; formamide, which can be a liquid component of a nucleic acid hybridization reaction; piperidine, which is a liquid component of a nucleic acid sequencing reaction; or any other non-aqueous solvent or other liquid component. A liquid can contain dissolved or suspended components, which can be useful, for example, for initiating, terminating or changing the conditions of a reaction, thereby facilitating the performance of single tube reactions.

As used herein, the term "reaction mixture" refers to any solution in which a chemical, physical or biological change is effected. In general, a change to a molecule is effected, although changes to cells also are contemplated. A reaction mixture can contain a solvent, which provides, in part, appropriate conditions for the change to be effected, and a substrate, upon which the change is effected. A reaction mixture also can contain various reagents, including buffers, salts, and metal cofactors, and can contain reagents specific to a reaction, for example, but are not limited to, enzymes, nucleoside triphosphates and amino acids. For convenience, reference is made herein generally to a "component" of a reaction, wherein the component can be a cell or molecule present in a reaction mixture, including, for example, a biopolymer or a product thereof.

As used herein, the term "target site" refers to a specific locus on a solid support that can contain a liquid. A solid support contains one or more target sites, which can be arranged randomly or in ordered array or other pattern. In particular, a target site restricts growth of a liquid to the "z" direction of an xyz coordinate. Thus, a target site can be, for example, a well or pit, a pin or bead, or a physical barrier that is positioned on a surface of the solid support, or combinations thereof such as a beads on a chip, chips in wells, or the like. A target site can be physically placed onto the support, can be etched on a surface of the support, can be a "tower" that remains following etching around a locus, or can be defined by physico-chemical parameters such as relative hydrophilicity, hydrophobicity, or any other surface chemistry that allows a liquid to grow primarily in the z direction. A solid support can have a single target site, or can contain a number of target sites, which can be the same or different, and where the solid support contains more than one target site, the target sites can be arranged in any pattern, including, for example, an array, in which the location of each target site is defined.

As used herein, the term "predetermined volume" is used to mean any desired volume of a liquid. For example, where it is desirable to perform a reaction in a 5 microliter volume, 5 microliters is the predetermined volume. Similarly, where it is desired to deposit 200 nanoliters at a target site, 200 nanoliters is the predetermined volume.

As used herein, a small volume, typically refers to a volume on the order of nanoliters, preferably less than 1 microliter and typically, less than 0.5 microliters and less. The term nanoliter volume refers to a volume of about 0.1 to about 1000 nanoliters, preferably about 1 to 100 nanoliters.

As used herein, symbology refers to the code, such as a bar code, that is engraved or imprinted on a surface. The symbology is any code known or designed by the user.

As used herein, a bar codes refers any array of, preferably, optically readable marks of any desired size and shape that are arranged in a reference context or frame of, preferably, although not necessarily, one or more columns and one or more rows. For purposes herein, the bar code refers to any symbology, not necessary "bar" but may include dots, characters or any symbol or symbols.

As used herein, the disclosed systems and methods generally are useful where the reaction volume is about 500 milliliters or less; are more useful where the reaction volume is about 5 milliliters or less; are most useful where the reaction volume is in the "submilliliter" range, for example, about 500 microliters, or about 50 microliters or about 5 microliters or less; and are particularly useful where the reaction volume is a "submicroliter" reaction volume, which can be measured in nanoliters, for example, about 500 nanoliters or less, or 50 nanoliters or less or 10 nanoliters or less, or can be measured in picoliters, for example, about 500 picoliters or less or about 50 picoliters or less. For convenience of discussion, the term "submicroliter" is used herein to refer to a reaction volume less than about one microliter, although it will be readily apparent to those in the art that the systems and methods disclosed herein are applicable to subnanoliter reaction volumes as well.

As used herein, a room refers to a space, such as a room, chamber or a hood or other enclosure that is in some manner separated. In an embodiment herein, the APL system is designed to operate in two rooms, such that manipulations that require sterile conditions can be performed in one room or chamber. Manipulations that do not require such conditions can be performed in a second room. Samples can then be automatically transported between the first room and second room. As desired additional rooms, with conditions designed for a particular set of manipulations may be included in the system.

Automated Process Line

In the Automated Process Line (APL) constructed in accordance with the disclosure herein, one or more robotic systems under computer control are used to manipulate the sample of interest. The robot(s) are commanded by controlling software and move the sample between the series of reaction and sample preparation stations that comprise the APL. The robot includes a robotic arm that moves, for example, along a track or on a central pivot, and is typically outfitted with a "gripper" arm, allowing it to grip reaction vessels and transport them between stations. Such robotic systems are commercially available and are commonly known to those of skill in the art. For example, a robotic system and accompanying software can be obtained from Robocon Labor-und Industrieroboter Ges.m.b.H of Austria ("Robocon"). In a preferred embodiment, the APL includes a Robocon "Model CRS A 255" robot, equipped with a "Digital Servo Gripper" mechanism, also available from Robocon. The robotic systems are designed such that they can be integrated with other computer-controlled instrumentation to perform consecutive operations to effect a multi-step process.

In the preferred embodiment, one robot moves along a central track in a contamination-controlled environment, such as a positive airflow or laminar flow chamber, to perform a series of manipulations or reactions on a biological sample. Once these steps are completed, the sample enters a second contamination-controlled environment, which serves as an antechamber into a non-sterile environment. The second environment can be sealed off from the first contamination-controlled environment and/or the non-sterile environment. For example, in a particular embodiment, the sample is transported from the contamination-controlled laminar flow chamber into a transport chamber, or taxicab. If desired, the taxicab can provide a sterile environment.

Upon entry of the sample into the transport chamber, the contamination-controlled environment is sealed off. The sample then moves along a pneumatically-driven or motor-driven stage in the transport chamber, and the transport chamber then opens up into the, non-sterile environment, such as an open room. In the open room, a second robot, also moving along a central track, takes control of manipulating the sample.

The sample to be analyzed is contained within a reaction vessel that is designed to integrate with all of the components of the APL and which is amenable to the conditions of the chemical or biological reactions performed. Preferred for high throughput analysis are reaction vessels that are capable of containing multiple samples, such as multiwell microtiter plates, preferably 96-well or 384-well plates or chips, such as silicon microchips. The reaction vessels also can comprise flat chips with reaction sites which are not wells, but physical locations that contain the reaction using a chemical barrier. In certain embodiments, the robot and/or gripper is adapted to hold a sample vessel. For example, pins may be added to the gripper in alignment with the wells of a microtiter plate for transporting the sample.

In high-throughput applications, where multiple sample plates are to be analyzed successively in an automated fashion, the samples can be held in a sample storage system, or rack, where they are picked up by the system robot and processed. An example of such a sample storage system, for use with multi-well microtiter plates, is the Robocon "Plate Cube" system.

In steps where sample vessels are to be sealed, such as when subjected to PCR amplification, or unsealed, such as for reagent addition or removal, an automated lid application/removal and sealing system may be integrated into the system. Examples of these include a lid parking station, such as is available from Robocon, and a plate sealer, such as the "MJ Microseal", available from MJ Research. A system turntable might also be employed to assist the system robot in orienting the samples for delivery into each station of the APL. Such a turntable is available, for example, from Robocon. Additionally, a shaker is also included in the APL system in embodiments where beads or other reagents are added to the sample for immobilizing the sample, or where other manipulations requiring mechanical shaking are involved.

In preferred embodiments, the sample plate or vessel is coded with a symbology, such as a bar code, which can be read by a reader, to allow sample tracking. In the preferred embodiment, separate bar code readers are contained in the contamination-controlled and non-sterile environments. Bar code systems, including one and two dimensional bar codes, readable and readable/writable codes and systems therefor, are widely available, such as from Datalogic S.p.A. of Italy ("Datalogic"), and are well known to those skilled in the art.

Sample handling and reagent additions are accomplished using automated liquid handling systems. These include systems capable of automatically dispensing liquids into the sample vessel, such as through a pipette, and can be adapted to any sample format, such as a multiwell microtiter plate. Such systems are commercially available, such as from Tecan AG of Switzerland ("Tecan") or Beckman Coulter, Inc. In a preferred embodiment, Tecan "Genesis 200/8" (200 cm with including an 8-tip arm) liquid handling systems, as well as a Beckman Coulter "Multimek 96" automated pipettor are used for liquid handling. Other liquid dispensing systems are described in allowed U.S. application Ser. Nos. 08/787,639, 08/786,988, and published International PCT application No. WO 98/20166, which are incorporated herein by reference.

Also present in the system may be an apparatus for preparing a test sample for analysis, including, for example, reagent addition means, or other means for performing reactions or processes to prepare the sample for analysis. In certain preferred embodiments, where mass spectral analysis, specifically MALDI-TOF analysis, is to be performed using a sample array, a matrix material (i.e., an organic acid) is added to the sample using an adapted piezoelectric pipetting dispensing system. The dispensing system includes a hydrophobic tip, which is capable of dispensing submolar, preferably nanomolar, samples. Such systems, as well as methods for preparing and analyzing low volume analyte array elements, have been described in allowed U.S. patent application Ser. Nos. 08/787,639, 08/786,988, and published International PCT application No. WO 98/20166, see, also Little et al., Anal. Chem. 1997, 69, 4540–4546, the contents of which are incorporated by reference herein in their entirety.

Alternatively, a system that dispenses liquid samples from the picoliter up to the nanoliter range is commercially available, such as the "Nano-Plotter" product from GeSiM GmbH of Germany ("GeSiM"). In other embodiments, reactions such as radiolabeling or adding a mass tag to the sample may be performed by the sample preparation apparatus.

A sample may also be transferred to or placed in a particular sample analysis vessel for analysis. The particular type of sample analysis vessel used is determined by the analytical method to be employed. For example, in a preferred embodiment, where mass spectrometry (MALDI-TOF) is used for analysis of a sample, a typical sample vessel is a silicon microchip (<1 square inch) that includes one or more, 100, 200, 300, 400, 500, up to 999 diagnostic sites, or even higher density, on a single chip, preferably in the pattern of a 2-D array. The chip, or multiple chips, can then be placed on a sample platform, designed specifically to be inserted into the mass spectrometer.

In a preferred embodiment, the analytical system is a MALDI-TOF mass spectrometer. A preferred mass spectrometer is manufactured by Bruker-Franzen Analytik GmbH of Germany ("Bruker") and uses a UV laser. In the spectrometer, a brief pulse of laser irradiation is absorbed by the matrix, leading to spontaneous volatilization and ionization of the matrix and DNA fragments. The molecular weight of the gas-phase ions are then determined by measurement of the time-of-flight of ions, which is proportional to their mass.

It should be understood that the nature of the sample to be analyzed and the analysis to be performed, as well as the feasibility of automating a reaction process, determine the components integrated into the APL, and the system is not to be limited to the particular embodiments described herein.

Module for Performing the Reaction in an Unsealed Environment

Systems for performing a reaction in an unsealed environment are provided in copending U.S. application Ser. No. 09/266,409, filed Mar. 10, 1999. These systems may be integrated into the APL provided herein. Briefly the systems and methods provide a means of maintaining a volume of a liquid, for example, a reaction mixture, present in an unsealed environment and, therefore, susceptible to loss of volume by evaporation. The liquid generally is present on a surface of a solid support, at a target site, and the environment into which evaporation can occur is air. The systems and methods provide a means to maintain a volume of a liquid at a predetermined volume, where the volume otherwise would decrease below the predetermined volume due to evaporation. These systems include a support for performing the reaction; a nanoliter dispensing pipette for dispensing an amount of a liquid onto the surface of the support; a temperature controlling device for regulating the temperature of the support; and means for controlling the amount of liquid dispensed, wherein the amount of liquid dispensed corresponds to the amount of liquid that evaporates from the support, wherein the system is not sealed.

Analytical Methods

The APL system can be used to perform a number of different reactions, dependent upon the nature of the sample and the analysis to be performed. The system is typically used to perform analysis on biological samples, typically biopolymers, including nucleic acids, proteins, peptides and carbohydrates. Methods of analysis of the biological samples include all known methods of analysis, including, but not limited to mass spectrometry (all light wavelengths), radiolabeling, mass tags, chemical tags, fluorescence, and chemiluminescence.

In a preferred embodiment, the sample is a purified previously amplified portion of genomic DNA or genomic DNA sample. For analysis of DNA samples, reactions such as nucleic acid amplification (e.g., PCR, ligase chain reaction) and enzymatic reactions, such as primer oligonucleotide base extension (PROBE), nested PCR or sequencing, may be performed. In addition, the apparatus can be used for hybridization (sequencing and diagnostic) reactions, and endo- and exonuclease mapping of biopolymers.

In certain embodiments, the sample may be immobilized on a solid support during all or part of the automated process. For example, enzymatic reactions, including diagnostics, such as a method designated primer oligo base extension (PROBE; see, e.g., published International PCT application No. WO 98/20019), nested PCR, sequencing, and other analytical and diagnostic procedures that are performed on solid supports (see, e.g., U.S. Pat. No. 5,605, 798). Briefly PROBE uses a single detection primer followed by an oligonucleotide extension step to give products, which can be readily resolved by MALDI-TOF mass spectrometry. The products differ in length by a number of bases specific for a number of repeat units or for second site mutations within the repeated region. The method is exemplified using as a model system the AluVpA polymorphism in intron 5 of the interferon-α receptor gene located on human chromosome 21, and the poly T tract of the splice acceptor site of intron 8 from the CFTR gene located on human chromosome 7. The method is advantageously used for example, for determining identity, identifying mutations, familial relationship, HLA compatibility and other such markers, using PROBE-MS analysis of microsatellite DNA. In a preferred embodiment, the method includes the steps of a) obtaining a biological sample from two individuals; b) amplifying a region of DNA from each individual that contains two or more microsatellite DNA repeat sequences; c) ionizing/volatilizing the amplified DNA; d) detecting the presence of the amplified DNA and comparing the molecular weight of the amplified DNA. Different sizes are indicative of non-identity (i.e. wild-type versus mutation), nonheredity or non-compatibility; similar size fragments indicate the possibility of identity, of familial relationship, or HLA compatibility. More than one marker may be examined simultaneously, primers with different linker moieties are used for immobilization.

As noted solid supports include, but are not limited to, flat surfaces, microtiter plates, beads, wafers, chips, and silicon support. Compositions and methods for immobilizing nucleic acids to solid supports, including methods for high density immobilization of nucleic acids are described in U.S. patent application Ser. Nos. 08/746,055 and 08/947,801 and published International PCT application No. WO 98/20166. Linkers for immobilizing nucleic acids to solid supports are well known. Linkers may be reversible or irreversible. A target detection site can be directly linked to a solid support via a reversible or irreversible bond between an appropriate functionality (L') on the target nucleic acid molecule (T) and an appropriate functionality (L) on the capture molecule (FIG. 1B). A reversible linkage can be such that it is cleaved under the conditions of mass spectrometry (i.e., a photocleavable bond such as a charge transfer complex or a labile bond being formed between relatively stable organic radicals).

Photocleavable linkers are linkers that are cleaved upon exposure to light (see, e.g., Goldmacher et al. (1992) *Bioconj. Chem.* 3:104–107), thereby releasing the targeted agent upon exposure to light. Photocleavable linkers that are cleaved upon exposure to light are known (see, e.g., Hazum et al. (1981) in *Pept., Proc. Eur. Pept. Symp. 16th*, Brunfeldt, K (Ed), pp. 105–110, which describes the use of a nitrobenzyl group as a photocleavable protective group for cysteine; Yen et al. (1989) *Makromol. Chem* 190:69–82, which describes water soluble photocleavable copolymers, including hydroxypropylmethacrylamide copolymer, glycine copolymer, fluorescein copolymer and methylrhodamine copolymer; Goldmacher et al. (1992) *Bioconj. Chem.* 3:104–107, which describes a cross-linker and reagent that undergoes photolytic degradation upon exposure to near UV light (350 nm); and Senter et al. (1985) *Photochem. Photobiol* 42:231–237, which describes nitrobenzyloxycarbonyl chloride cross linking reagents that produce photocleavable linkages), thereby releasing the targeted agent upon exposure to light. In preferred embodiments, the nucleic acid is immobilized using the photocleavable linker moiety that is cleaved during mass spectrometry. Exemplary photocleavable linkers are set forth in published International PCT application No. WO 98/20019. Bead linkers for immobilizing nucleic acids to solid supports are described in allowed U.S. application Ser. No. 08/746,036 and published International PCT application No. WO 98/20166 and WO 98/20020.

Preferred applications include, but are not limited to, sequencing and diagnostics based on analysis of nucleic acids and polypeptides or diagnostics by mass spectrometry. Preferred mass spectrometric methods include ionization (I) techniques including, but not limited to, matrix assisted laser desorption (MALDI), continuous or pulsed electrospray (ESI) and related methods (e.g. Ionspray or Thermospray), or massive cluster impact (MCI); the ion sources can be matched with detection formats including linear or non-linear reflectron time-of-flight (TOF), single or multiple quadruple, single or multiple magnetic sector, Fourier Transform ion cyclotron resonance (FTICR), ion trap, and combinations thereof (e.g., ion-trap/time-of-flight). For ionization, numerous matrix/wavelength combinations (MALDI) or solvent combinations (ESI) can be employed. DNA sequencing by mass spectrometry is described in U.S. Pat. Nos. 5,547,835; 5,691,141; and related U.S. application Ser. Nos. 08/467,208, 08/481,033 and 08/617,010 and in PCT patent application No. PCT/US98/26718, filed Dec. 15, 1998, published International PCT application Nos. WO 94/16101 and WO 97/37041.

DNA sequencing using mass spectrometry is described in U.S. Pat. No. 5,547,835. DNA sequencing by mass spectrometry via exonuclease degradation is described in allowed U.S. application Ser. No. 08/744,590, U.S. Pat. No. 5,622,824, published International PCT application No. PCT/US94/02938, U.S. Pat. Nos. 5,851,765, and 5,872,003. Processes for direct sequencing during template amplification are described in allowed U.S. patent application Ser. No. 08/647,368^C and published International PCT application No. WO 97/42348.

DNA diagnostics based on mass spectrometry are described in U.S. Pat. No. 5,605,798 and published International PCT application Nos. WO 96/29431 and WO 98/20019. Diagnostics based on mass spectrometric detection of translated target polypeptides are described in U.S. application Ser. No. 08/922,201 and published International PCT application No. WO 99/12040. Mass spectrometric detection of polypeptides is described in U.S. patent application Ser. No. 08/922,201 and U.S. application Ser. No. 09/146,054.

It is understood that the nature of the sample to be analyzed and the analysis to be performed, as well as the feasibility of automating a reaction process, determine the methods used in the APL, and the methods are not to be limited to the particular embodiments described herein. Any method and process that requires small volumes and involves one or more steps in the exemplified embodiment may be adapted and used in an APL as described herein.

Exemplary Embodiment

One preferred embodiment, which is a dual space system, integrates nucleic acid amplification (via PCR), immobilization of the nucleic acid on a solid support, followed by enzymatic reaction (e.g., PROBE, mass array, sequencing, nested PCR), sample conditioning, addition of an organic acid matrix for MALDI-TOF analysis and MALDI-TOF analysis on a microchip. This embodiment is described with respect to the Automated Process Line (APL) system 100 depicted in FIG. 1. As noted above, samples are initially prepared in a contamination-controlled environment 102, such as a clean room or laminar flow room, and are moved by a sterile transport chamber 104 or taxicab into a non-sterile environment 106. In FIG. 1, samples are indicated by rectangular elements with criss-crossed lines.

In the FIG. 1 embodiment, sample preparation begins in a Liquid Handling System 108, such as the Tecan "Genesis 200/8 Robotic Sample Processor" product. One or more samples 110 of purified genomic DNA are delivered by a robot 112 to 96-well or 384-well microtiter plates 114 in the Liquid Handling System 108, preferably using a 200 cm instrument width and an 8-tip arm. These sample processing steps occur in the contamination-controlled environment 102. Multiple samples may be included in the APL system for high-throughput processing. These samples may, at times during processing, be held in a sample storage apparatus, such as the "Plate Cube" rack 116 available from Robocon. To the sample plates 114 are added a PCR reaction mix 118, including PCR primers, where one of the primers is labeled at the 5' end with functionality, such as biotin, that can be used to immobilize the amplicon to a solid support is added to the sample mixture. Where multiple samples are to be processed, a wash solution is contained in a reservoir 120 and is used to clean the pipette tips to prevent cross-contamination between samples or reagents. Alternatively, the APL system can process multiple samples using disposable pipette tips.

The sample plates are manipulated by a robotic system, for example the Robocon robot 112, such as the CRS A 255 Robot, which moves along a central track 122. The robot 112 operates under control of a clean room control system computer 124 that includes a central processing unit (CPU) 126, a operator interface 128, and an APL interface 130. The CPU can comprise any commercially available desktop computer, such as an IBM-compatible personal computer (PC) or the like.

The operator interface 128 includes a visual display and keyboard or other device through which an operator provides commands. The APL interface 130 is an interface between the computer and the process line, through which the computer 124 controls the robot. The APL interface may include, for example, a robot control program installed in the computer 124 and available from Robocon for control of its robot products. An optional second computer 131 can assist the first computer 124 in performing clean room processing.

The robotic arm is equipped with a gripper 132, such as the "Digital Servo Gripper" arm, also available from Robocon, to pick up and drop off the sample plates 114 as needed, for processing. In a particular embodiment, a microtiter plate is aligned with the gripper so the plate receives pins 134 of the gripper, which more securely couple the plate with the gripper for more secure transport.

FIG. 1 shows a sample plate 140, including the sample and PCR mix, that is moved to a turntable 142 and oriented such that the robot picks it up and moves it to a bar code reader 144, for example, as is available from Datalogic, where the bar code is read and recorded for sample tracking. Sample tracking and reorientation may be performed multiple times during sample processing to assist the robot in sample handling.

The sample plate 140 is reoriented by the robotic arm, using the turntable, and is then placed in a lid parking station 146, such as is available as a robotic module in the Robocon robotic system. At the lid parking station, a lid may be parked or retrieved. In the preferred embodiment, the lid is a solid structure, such as a metal lid, with a flexible seal such that placing the lid on the plate seals the contents of the plate. The sealing eliminates evaporation during subsequent processing, such as PCR amplification. Such a sealing apparatus, known as "MJ Microseal", is available from MJ Research, Inc. Alternatively, after the sample plate is reoriented, it can be penetrably sealed. For example, the sample plate can be covered with a foil wrap that can later be penetrated by test probes or the like. A similar penetrable seal can be provided by a parafilm that is attached to the plate by heat, or other plastic or wax based sealers.

The sealed sample plate is then picked up by the robotic gripper arm and transported from the laminar flow environment 102 into the taxicab transport station 104, which provides a sterile environment. First, an entry door opens in the taxicab to permit the robot to place the sample plate into the taxicab. Once in the taxicab 104, the entry door closes behind the sample to prevent contamination. Within the taxicab transport station 104, the sample plate is placed onto and is transported along a pneumatically driven stage, and a second door opens to permit the sample to exit the taxicab into a non-sterile environment. Once outside the sterile taxicab environment, control of sample manipulation is transferred to a second robot 150, also equipped with a gripper 152 and moving along a center track 153. The sample plate is transported by the robot 150 and is read by a second bar code reader 154 for sample tracking. The second bar code reader 154, as well as a second turntable 156, lid park station 158 and sample storage rack 160 are included outside the contamination-controlled area 102 for more efficient sample handling.

The robot 150 operates under control of a PCR Room computer 161 that has a construction similar to the Clean Room computer 124. Thus, the PCR Room computer 161 can comprise any commercially available desktop computer that can interface with the APL system process line and stations.

After the sample identification code has been read by the bar code reader 152, the sample plate is moved by the system robot 150 to a PCR station 162, where amplification is carried out. The amplification reaction can be PCR, ligase chain reaction, etc. In a preferred embodiment, the "MJR Tetrad" thermocycler, available from MJ Research, Inc., is used for PCR amplification. Other PCR thermocycler systems are commonly known to those of skill in the art and may optionally be integrated into the system. Methods for DNA amplification are well known to those of skill in the art. Multiplex PCR can also be carried out using the system.

After PCR amplification, the plates are removed from the PCR reaction station 162 by the robot 150. The plates are then moved to the lid park station 158, where the lids are removed and unsealed. As noted above, however, a penetrable seal such as a foil wrap or parafilm is an alternative to a lid seal, and if removable lids are not used to seal the plates, then the lid park station is unnecessary and the next substance that must be added to the wells of the plate will be inserted upon piercing of the foil wrap.

Alternatively, using a second liquid handling system 164, preferably a Tecan "Genesis 200/8" system, streptavidin-coated paramagnetic beads can be loaded from a reservoir 166 and mixed with the PCR-amplified DNA in the sample plate, resulting in immobilization of the amplicon via the functionalized (e.g. biotinylated) primer. Beads are used, for example, where the samples are contained in multiwell microtiter plates. The beads and PCR products are reacted by shaking, using a shaking apparatus 168, such as is available from Robocon, and which is integrated into the APL system.

The sample plates are then moved to a liquid handling and mixing station 170, into which a magnetic lift station 172 has been incorporated, for post-PCR processing. In a preferred embodiment, the liquid handling station is a "Multimek 96" well pipetting station, available from Beckman. The magnetic lift applies magnets to the sample plate by moving the magnets up against the bottom of the sample plate, for example, by using a pneumatic lift, thereby immobilizing the DNA and beads, and the supernatant is removed. The magnets are then released and liquid is added to the wells to resuspend the sample. Alternatively, the sample plate could be moved, for example, by the robot to bring it into contact with the magnet. The magnet can be a solid surface that interacts with the entire bottom of the sample plate, or can be designed to more specifically interact with the individual samples. For example, where the sample plate is a 96-well microtiter plate, the magnet can be configured as 8 or 12 individual strips so that each strip comes into contact with the bottom of a single row of wells.

Figure 2:
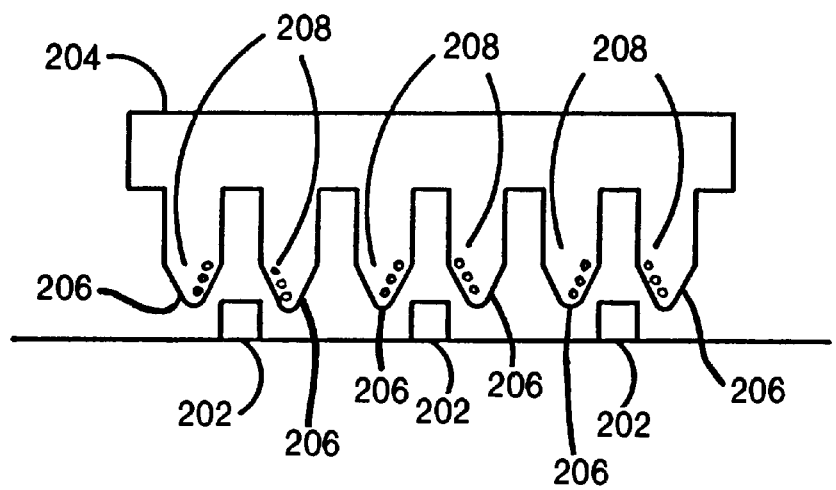
FIG. 2 shows a magnetic strip construction of the magnetic lift illustrated in FIG. 1.

Conventionally, the magnets of the magnet lift station 172 are elongated, strip magnets arranged in rows between sample wells. Alternatively, the magnets can be configured as individual point magnets, for example, as disk-shaped magnets arranged into an 8×12 grid of magnets that correspond to the positions of the sample wells in a 96-well microtiter plate. This configuration provides an advantage over the magnetic strip configuration, particularly where small volumes are to be added to the sample. For example, as illustrated in FIG. 2, where magnetic strips 202 are used with a multiwell microtiter plate 204, the magnet strips are offset from the center of the sample wells 206, and magnetic beads 208 concentrate along the sides of the wells.

Figure 3:
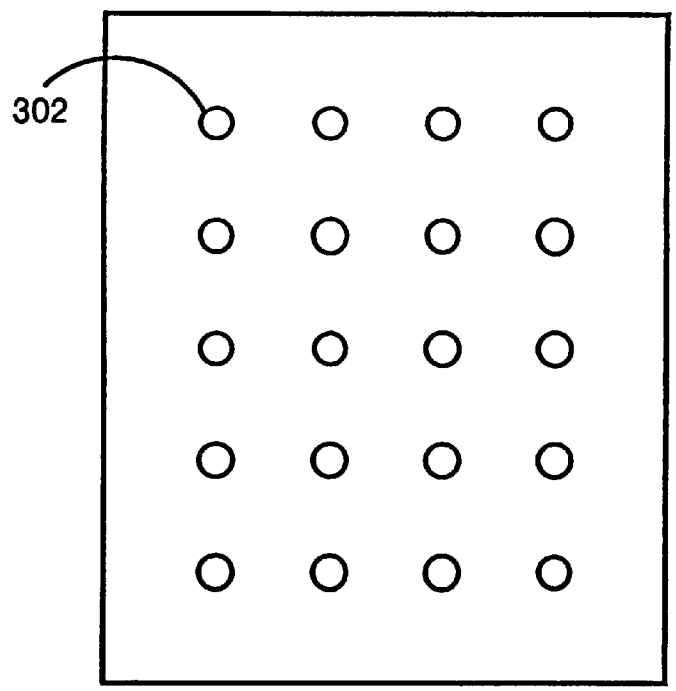
FIG. 3 shows a point-magnet construction of the magnetic lift illustrated in FIG. 1.

It is desirable that all beads be concentrated in a location such that added liquid makes maximum contact with the samples. If, for example, a volume of sample is removed from the wells and a smaller volume is to be subsequently added, the smaller volume might not be sufficient to wash all the beads from the side of the wells, and the sample concentration could be affected. FIG. 3 is a plan view of the alternative, preferred embodiment, and shows a portion of the construction that centers a disk-shaped point magnet 302 beneath the center of each sample well in a multiwell microtiter plate. For simplicity of illustration, only a 4×5 grid is shown. It should be apparent that by using individual point magnets at the bottom of the wells, the beads collect at the bottom of the wells and are more easily resuspended, particularly where a smaller volume of liquid is to be added. Multiple rounds of liquid handling are employed to allow for supernatant removal, denaturation of double stranded DNA, wash steps and the addition of enzymatic reaction reagents (PROBE).

Returning to FIG. 1, a sample plate 176 is next moved by the robotic system to the lid park station 158, and sealed with a lid. This operation is optional and is used, for example, when the sample is subjected to high temperatures in order to prevent evaporation. The sample plate can otherwise remain open to the environment.

The robot 150 moves the sample plate again to the PCR station 162 and places it into a thermocycler of the PCR station. The thermocycler carries out an enzymatic reaction. The enzymatic reaction can be, for example, PROBE, nested PCR, primer extension, or sequencing reactions (e.g. Sanger). Details for such enzymatic reactions are commonly known to those skilled in the art.

After the reaction is complete, the sample plate is removed from the thermocycler of the PCR station 162 and then is returned to the lid park station 158 by the robot 150, and the lids are removed and the plate unsealed.

The sample plates are again moved to the liquid handling and mixing station 170 containing the magnetic lift station 172, which applies the magnets, immobilizing the beads and DNA. The liquid handling and mixing station then removes the supernatant. The magnets are then released and liquid is added to the wells. Multiple rounds of liquid handling are employed to allow for washing steps or treatment with ammonium citrate, TRIS, or any other reagent that removes salt ions and replaces them with ammonium ions, thereby conditioning the samples prior to mass spectrometry. Once conditioned, the primer extension product is denatured from the immobilized DNA with ammonium hydroxide and released into the supernatant. The ammonium hydroxide reaction is performed for five minutes at approximately 60° F. The supernatant is removed to a clean sample plate and placed on a shaker 168.

The sample plate is next transported to a sample preparation station 178 to prepare it for analysis. In a preferred embodiment, where MALDI-TOF mass spectral analysis is performed, nanoliter or smaller volumes of sample are dispensed onto pre-made silicon chips to form a microarray and reacted with matrix. In general, however, the sample may involve any preparation for use with any analytical method. Nanoliter or smaller volumes are dispensed using piezoelectric pipette, such as the "Nano-Plotter" station, available from GeSiM. Finally, the sample plate is transported to the analytical system, e.g., a mass spectrometer or other spectrometric techniques, such as UV/VIS, IR, fluorescence, chemiluminescence or NMR spectrometry, where sample analysis is performed.

Several alternatives are possible for preparing a sample for analysis and loading the sample into the analytical system. For example, three separate components, including a dispensing apparatus, a sample platform containing test samples, and an analytical instrument, can be integrated into the APL system.

In a preferred embodiment, a nanoliter dispensing apparatus (nano-plotter) 180 of the sample preparation station 178 is used to prepare one or more samples for mass spectral (MS) analysis, preferably using MALDI-TOF MS. In preparing a sample for MALDI-TOF analysis, the sample is co-crystallized with a matrix material. The sample is then loaded into a mass spectrometer 182 on a MS sample platform. Alternatively, the MS platform may be integrated into the mass spectrometer, rather than a separately-controlled component. The sample platform can be adapted to hold one or more sample analysis vessels, such as microchips.

In another embodiment, the APL system can carry out enzymology directly on the beads and can directly add matrix to the beads to analyze using mass spectrometry, where the DNA is ionized directly off the beads. This eliminates the need for a nanoliter dispensing station 178 such as the GeSiM "Nano-Plotter", rather, matrix is added with the liquid handling system 170.

In a preferred embodiment, one or more microchips containing test samples are prepared by dispensing nanoliter volumes of a sample and an organic acid matrix onto a chip using a nanoliter dispensing apparatus 180, or a nano-plotter, and loading the chips into a mass spectrometer 182. Alternative embodiments are possible where (1) one or more test samples, e.q., on sample chips, are prepared on a sample platform on the nano-plotter and the sample platform is then transferred, e.g., by a robot, into the mass spectrometer; or (2) where one or more sample chips are prepared on the nano-plotter, transferred to a mass spectrometer sample platform station 184 and then inserted into the mass spectrometer.

In another embodiment, the APL system can carry out enzymology directly on a microchip by performing the steps of:
1. Aliquot genomic DNA and transfer to second chamber via taxi;
2. PCR amplify the genomic DNA using previously described steps;
3. Using a liquid handling apparatus (Tecan or GeSim) or pintool add DNA to microchip. The chips are held in a holder that can be manipulated by the robot;
4. Add PCR reaction mix to chip;
5. Incubate on thermocycler;
6. Wash chip with liquid handling apparatus;
7. Add matrix to chip;
8. Load chip in MALDI; and
9. Ionization/Desorption directly from the chip via MALDI.

Mass Spectrometer Interface

Figure 4:
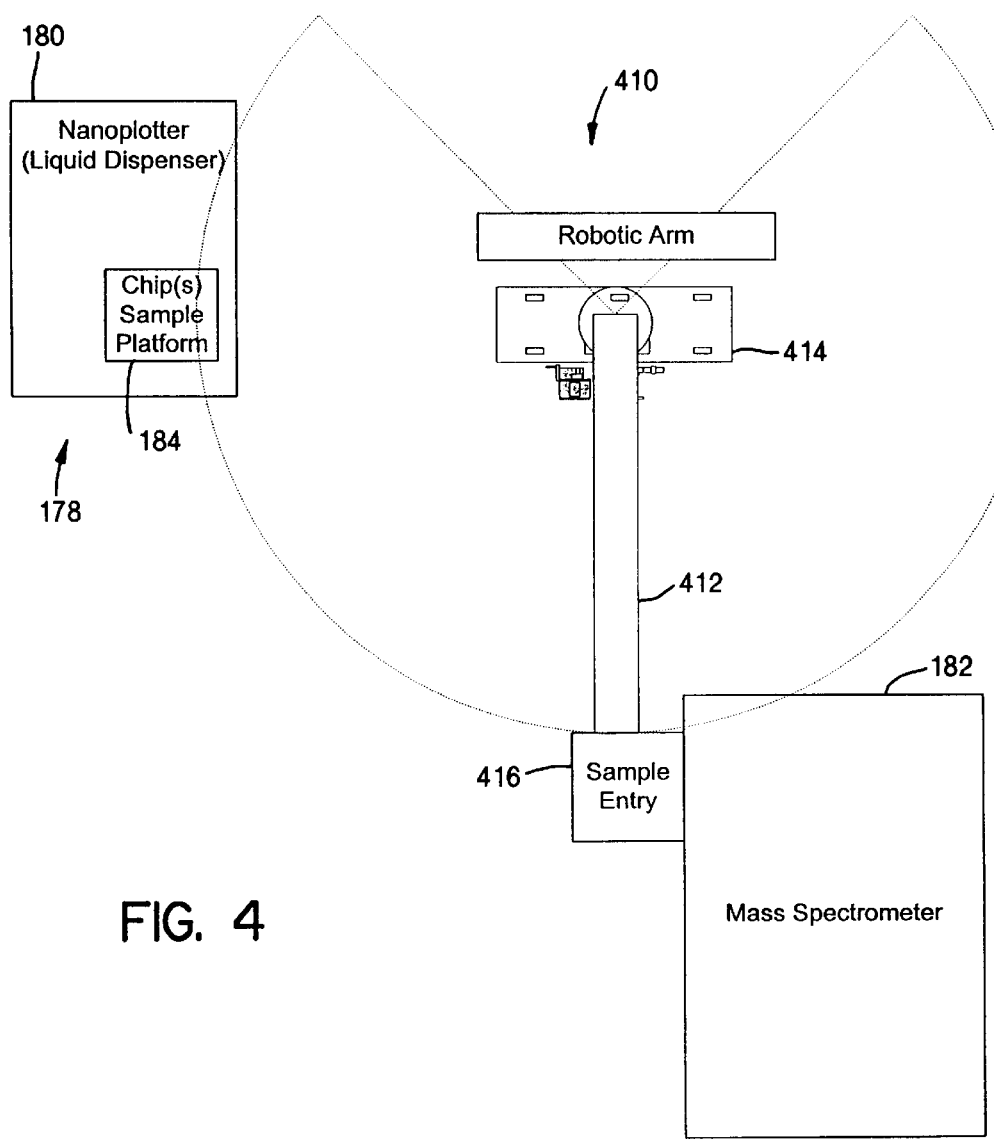
FIG. 4 shows the robotic interface between the chip processor and the mass spectrometer of the automated process line illustrated in FIG. 1.

The nano-plotter and mass spectrometer are integrated into the APL system 100 and communicate with each other, either directly or via a control computer. For example, in one embodiment, commands are automatically executed from a computer controller to initiate opening and closing of a mass spectrometer entry door (e.g., by using pneumatics or a motor-driven mechanism) and to initiate loading of a MS sample platform into the spectrometer (e.g., by using a robotic arm), where the platform is either loaded with sample chips directly on a nano-plotter 180, or the sample chips are prepared on a nano-plotter 180 and then are transferred onto a sample platform 184. FIG. 4 shows one implementation of the robotic interface between the nano-plotter and the mass spectrometer illustrated in FIG. 1.

In the FIG. 4 embodiment, the samples are automatically transported from the sample preparation station 178 to the mass spectrometer 182 by a robotic arm system 410 (not shown in FIG. 1). As described above, the samples are prepared for the mass spectrometer 182 in the nano-plotter 180 and/or the sample platform station 184. When preparation is complete, an arm 412 rotates about a pivot base 414 to pick up the samples from the sample preparation station and then positions them at a sample entry station 416 of the mass spectrometer.

Data Analysis

Conventionally, the output of mass spectrometer testing is analyzed by an individual datum-by-datum, so that an individual examines the output of a sample test and makes a conclusion about the test, sample-by-sample. In the Automated Process Line (APL) described above, the volume of test results is sufficiently large that any individual analyzing the mass spectrometer output would quickly be unable to keep up with the APL output pace. The APL system of the preferred embodiment performs computer-automated analysis of mass spectrometer output data to determine genotype or make another analysis as quickly as the system produces test results. The data analysis can continue as long as the system is in operation, including on a round-the-clock, 24-hour basis. The APL system performs the test output analysis by automatically processing the mass spectrum output data of a sample, comparing the output data against expected spectrum output values for different genotypes, producing a conclusion about the sample genotype based on a conclusion about most likely genotype for the sample, and continuing with the output data of the next sample.

In the preferred embodiment illustrated in FIG. 1, the data analysis is performed by a dedicated data analysis computer 188 that receives output data from the mass spectrometer 182 and any other pertinent APL stations or components. The data analysis computer can comprise any commercially available desktop computer, and can have the same configuration and components as the Clean Room control computer 124 described above. Thus, the data analysis computer 188 includes a CPU having an operating environment in which programs are executed, and also includes an operator interface with a keyboard and a display.

The process line 100 operates continuously until a stop command is received, for a high sample throughout. Therefore, the process line provides for emergency situations where an immediate halt is required by providing halt switches 198 placed around the line. The system also can be halted by a software halt command that is input by an operator at any of the control computers 124, 131, 161, 188. The sample preparation, testing, and data analysis otherwise continues unimpeded.

Figure 5:
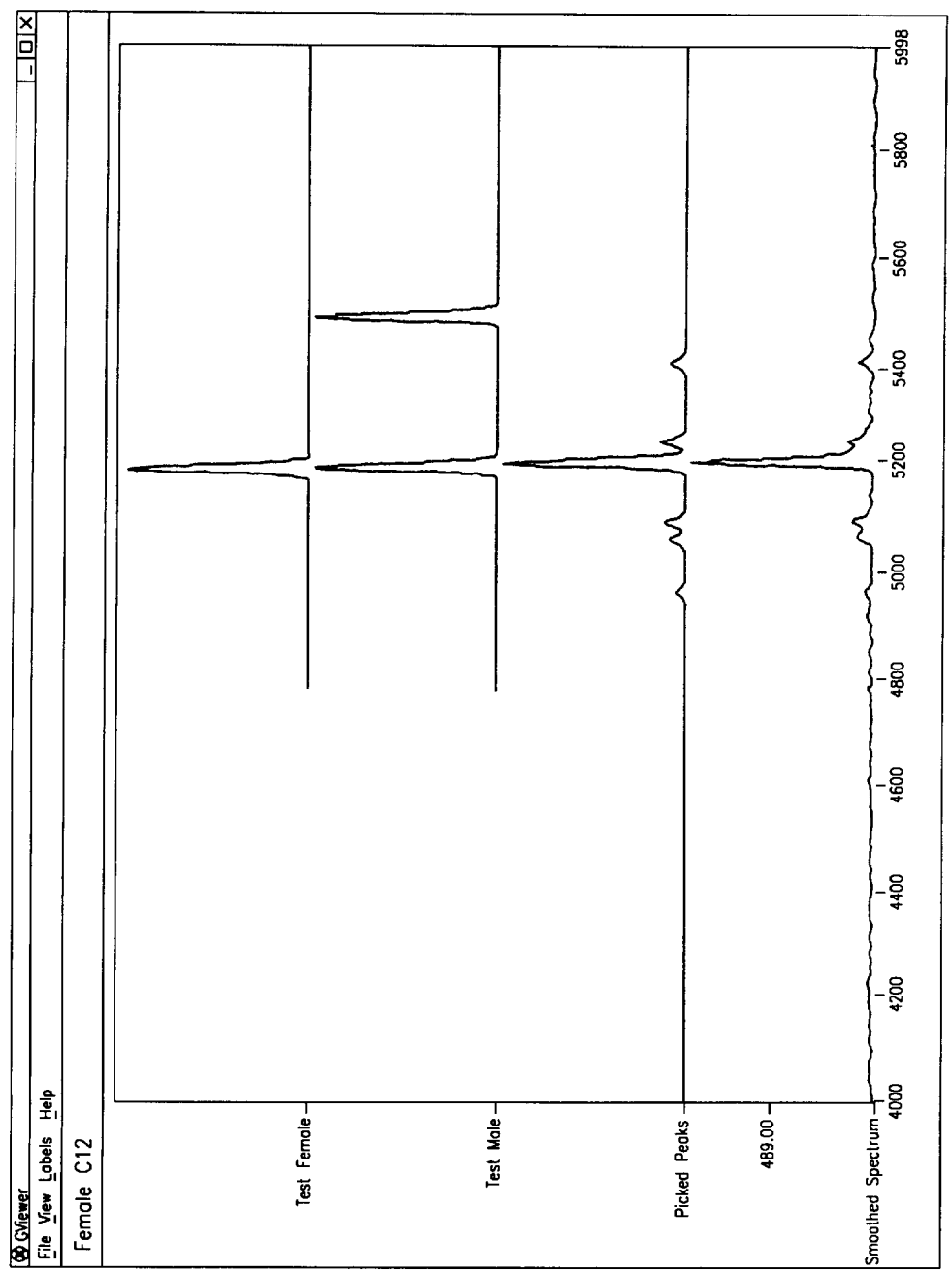
FIG. 5 shows a comparison of a mass spectrum of a test sample with stored spectra from samples with known genotypes.

A visual display of the data analysis is depicted in FIG. 5, which shows from top to bottom: a graph of two exemplary test spectra against which output data will be compared; a graph of output data picked peaks for analysis; and a graph of smoothed spectrum data. Those skilled in the art will appreciate that the spectra shown in FIG. 5 correspond to multiple graphs of mass spectrometer output, wherein the horizontal axis (x-axis) units are in mass per unit charge, also referred to as units of Daltons, and the vertical axis (y-axis) is in relative intensity of spectrometer discharge.

The exemplary spectra shown in FIG. 5 relate to male-female genotypes, but those skilled in the art will appreciate that any other paired-outcome typing decisions may be the subject of the sample analysis.

Figure 6:
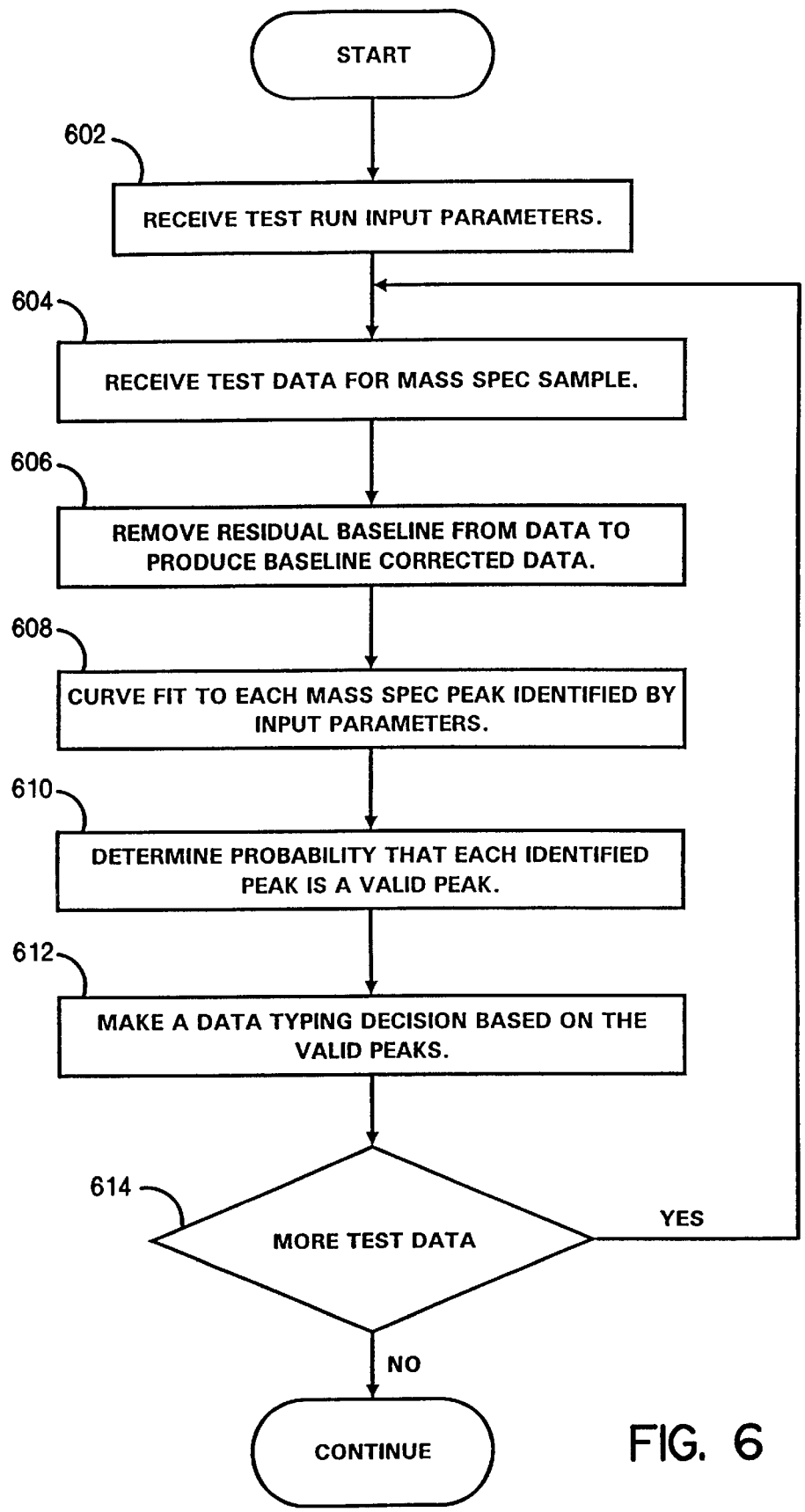
FIG. 6 is a flow diagram that illustrates the data analysis processing steps performed by the automated process line of FIG. 1.

In FIG. 5, the first test spectra is labeled "Test—Female" and corresponds to output spectra that might be expected from a female test subject. The second test spectra is labeled "Test—Male" and corresponds to output spectra that might be expected from a male test subject. Thus, the object of the APL processing will be to determine whether a given sample genotype belongs to a female subject or a male subject. The "Picked Peaks" of FIG. 5 spectra is a display of the mass spectrometer output for a particular sample over a predetermined range, to show particular output peaks. The output peaks shown in the Picked Peaks graph are selected by the APL system based on input parameters supplied by the APL operator, as described further below. The bottom spectra of FIG. 5 is a display of the spectra output after correction processing initiated by the APL system. It should be understood that the Test—Female and Test—Male graphs of the FIG. 5 display will not change as the APL system processes the mass spectrometer output data, while the Picked Peaks and Smoothed Spectrum graphs are different for each sample data, and therefore will generally change with each sample being processed. It also should be understood that the Picked Peaks and Smoothed Spectrum displays can be stopped on any one of the output graphs, if the operator wants to view one particular set of graphs. FIG. 6 is a flow diagram of the operating steps performed by the APL system in carrying out the mass spectrometer data analysis, and will be best understood with reference to the FIG. 5 graphs.

The first data analysis step, represented in FIG. 6 by the flow diagram box numbered 602, is to receive test run input parameters. These are parameters that the APL system will receive from an operator and will apply in processing a run of mass spectrometer output data. That is, the APL system will use the test run input parameters to evaluate test samples until the test run parameters are changed by the APL operator. As noted above, a test run might involve producing mass spectrometer output and analyzing it on a 24-hours-per-day basis. In the preferred embodiment, the operator provides the test run parameters through a graphical user interface using a display mouse and keyboard of the APL system. The test run input parameters received from the operator will include the x-axis range in Daltons for the spectrometer output data and x-axis locations of expected peaks that are picked for data identification and genotype evaluation. The input parameters will also include an expected baseline value, defining a noise floor above which data should comprise a peak.

In the next processing step, represented by the FIG. 6 flow diagram box numbered 604, test data is received for a particular test sample submitted to the mass spectrometer of the APL system. A particular test sample may be one well in a 96-well-by-96-well tray, for example. Other tray sizes may be accommodated by the APL.

Those skilled in the art will understand that a mass spectrometer bombards a crystalline-based sample with energy until the sample vaporizes and output products are produced. The output products consist of sample particles that are ionized and projected outwardly to different distances from the sample center. The mass spectrometer detects the distribution of output products having a particular mass per unit charge and assigns a relative intensity to those output products. The mass/charge units are given in Daltons or kiloDaltons (kD). Thus, the mass spectrometer output for a given sample is a sequence of paired numbers, or x-y values, that specify the detected mass/charge over a range of Daltons (x-axis) and the corresponding relative intensity (y-axis) distribution over that range.

For each set of sample data that is processed, the APL system removes the residual baseline. This processing is represented by the FIG. 6 flow diagram box numbered 606, and allows for a rolling baseline that might otherwise skew the output data. More particularly, with current processing systems, it is possible to misinterpret peaks or spikes, such as where true data peaks are located in valleys. Conventional programs identify peaks by detecting data intensity values (see FIG. 5) that are greater than a baseline value. The data, however, can contain localized areas in which a peak lies within a valley of a plateau area having an elevated baseline. Peaks that are in such valleys may be missed by conventional programs that do not detect a sufficient difference between the peak height relative to the plateau level. It has been found that such conventional programs may correctly identify peaks up to 80% of the time, but cannot generally provide greater accuracy due to missed peaks.

To remove the residual baseline and increase accuracy, the APL data analysis receives the input parameters that contain the operator's specification of where the peaks in the sample experimental results should be located in the mass spectrometer output. The APL system then examines the output data where there should be no peaks to find the true baseline value. The processing represented by the FIG. 6 flow diagram box numbered 606 therefore includes modeling the baseline of the mass spectrometer output with a quadratic equation, based on the test run inputs from the operator. It has been found that a quadratic equation is superior to using a cubic equation, and also closer than a lower-order fit, even though very small coefficients are expected for the baseline curve fit.

For example, the range of interest might be mass spectrometer output over the range of 4000 to 9000 Daltons. The maximum range and minimum range would be received as test run inputs. In addition, the expected peaks for the sample experimental data over that range of interest would be received as test run inputs. The data concerning expected peaks should include the peaks that will be produced given the data types for which there is testing, and also peaks expected in the output as a result of primer substances in the sample. Thus, the range of interest should include output artifacts from primer sources. These primer output artifacts can serve as landmarks to identify any output shifting. In addition to the locations of the expected peaks, the APL system also receives the peak width as in input test run parameter. The APL system assumes that peaks will be distributed as a gaussian curve, and the peak width input parameter indicates the approximate width for each of those peaks. In the preferred embodiment, there is one input for all peaks. For example, all peaks may be specified as having a width of 10 Daltons (ten x-axis units).

Next, with the test run parameters that specify the range of interest and the location of peaks, the APL system will identify peak-free regions in the mass spectrometer output of each sample that correspond to the range of interest, with the data at the peaks removed. For example, suppose there are two peaks of interest expected in the output that will identify a sample as being one genotype or another. Suppose also that there is an additional peak expected in the output, for primer output artifacts. Therefore, a total of three peaks will be expected in the mass spectrometer output over the range of interest. Then the peak-free regions would be those regions in the output data along the x-axis over the range of interest, with the data at the three identified peaks deleted. As noted above, the peaks are assumed to be gaussian, with a width value specified in the input parameters. Therefore, the data for deletion comprises the peaks identified in the test run input parameters and also an area two peak widths wide on either side of each identified peak (peak midline, +/- two peak widths).

It is the mass spectrometer output data with the peaks deleted that gives the peak-free region, to which the quadratic equation is fitted. Typically, the variable quadratic coefficients would be small, but it is possible to get contamination from the lower-mass sample particles, which can skew the output. If such contamination is present in the output, then the sample output may be skewed so that the peak free regions will be best modeled by a quadratic equation. It has been found that contamination products are best modeled with a quadratic equation, rather than a linear, cubic, or other type of equation.

The technique for determining the coefficients of the quadratic equation for the best fit to a peak-free baseline is preferably a least squares fit technique, which will be well-known to those skilled in the art. In particular, error minimization using gradient information has been found suitable for the least squares fit. Thus, the curve-fit quadratic baseline equation can be used to produce an expected baseline over the mass spectrometer output range of interest. Therefore, as part of the baseline correction processing represented by the FIG. 6 flow diagram box numbered 606, at each data point interval along the range of interest (e.g., from 4000 to 9000 Daltons), the curve-fit baseline equation is used to calculate a corrected baseline value, which is subtracted from the sample data. The baseline correction occurs over the entire data range, including at the peaks. This produces a new set of baseline-corrected sample data values, i.e., a baseline-corrected output spectrum.

In the next processing step, represented by the FIG. 6 flow diagram box numbered 608, a curve is fit to each baseline-corrected peak value in the mass spectrometer output data. In the preferred embodiment, a standard curve fitting algorithm is used, such as the Marquardt-Levenberg algorithm. This fits a gaussian curve to each possible baseline-corrected output peak position. Those skilled in the art will understand that the output of such curve fitting will provide coefficients of a gaussian distribution centered at each peak that will match the height of the baseline-corrected output data at that peak, and will also provide the covariance of the curve-fit height. Thus, the box 308 curve fitting will provide, for each peak, equation coefficients that give a peak height and a covariance for the equation at that peak.

In the preferred embodiment, the "Picked Peaks" graph in FIG. 5 represents all peaks in the mass spectrometer output that have a height that exceeds the baseline corrected value generated by the box 606 processing, using peaks that are modeled from the box 608 processing. Alternatively, the Picked Peaks graph may represent the peaks in the actual mass spectrometer output that exceed an input threshold value. This latter type of Picked Peaks graph display is the type that is typically provided by mass spectrometer manufacturers, such as Bruker-Franzen Analytik GmbH ("Bruker") of Germany. In the preferred embodiment, the "Smoothed Spectrum" graph of FIG. 5 represents the output from the mass spectrometer with default data processing, which may include curve smoothing or other data processing provided by the mass spectrometer manufacturer. This type of Smoothed Spectrum graph is provided, for example, as standard output from the Bruker mass spectrometer. Alternatively, the Smoothed Spectrum graph may represent the mass spectrometer output with the baseline threshold parameter subtracted, or the actual mass spectrometer output with the quadratic-fit baseline curve subtracted.

In the next processing step, represented by the FIG. 6 flow diagram box numbered 610, the APL system determines the probability that the output data at each identified peak location is a valid peak. In the preferred embodiment, the peak validation decision is made by comparing probability density functions (PDF) for the peak-free region and for the fitted peak by constructing gaussian (or normal) probability curves and comparing them to determine if the data overlaps. If the two curves (the fitted peak and the peak-free region) are substantially free of any overlap, then the APL assumes that a true peak has been identified. Otherwise, the fitted "peak" is considered a spurious datum in the noise of the mass spectrometer output.

More particularly, the PDF of the peak-free region is assumed to be a gaussian distribution. The mean height and the standard deviation are determined by the mass spectrometer output for the sample in question. The PDF at each identified peak location is assumed to be a gaussian distribution with the mean height and the standard deviation given by the curve fitting algorithm described in box 308. The second gaussian curve will be determined once for each peak. The degree to which the two curves resemble each other is compared statistically using hypothesis testing that will be well-known to those skilled in the art. The output of the hypothesis test will be a probability value (from zero to one) that characterizes the peak under consideration. Thus, each peak is assumed to be an independent statistical event.

For example, the comparison uses the baseline curve, which is a quadratic model (peak-free region) having a particular mean height and corresponding standard deviation. The comparison also uses the gaussian model of each peak, having a mean height and standard deviation. If the mean values of the two respective curves are different by more than two standard deviations, then it is assumed there is no overlap for purposes of peak validation. That is, the test peak is a valid peak. If the two curves are not different in mean by more than two standard deviations, then the identified peak is not a valid peak, but is part of the output noise.

After the APL system evaluates the probability for all of the peaks, it will know the number of peaks that have been identified as valid. The system then determines probabilities for the genotypes under consideration. The APL system makes a data typing decision based on the presence or absence of sufficient true or validated peaks to indicate one genotype or the other. This processing is indicated in FIG. 6 by the flow diagram box numbered 612, and is carried out in a probabilistic manner.

For example, suppose a sample is to be typed as either female or male, and a female is indicated by the presence of an output peak at a position "A" and the absence of an output peak at a position "B", while a male is indicated by a peak at position "A" and also at position "B". Then the probability of a sample being female is the product of the probability of a true peak occurring at A and the probability of a peak not occurring at B. Stated in equation form:

$$P(\text{female})=P(A)*(1-P(B)).$$

The probability of a sample being male is then the product of the probability of a true peak occurring at position A and the probability of a true peak occurring at position B, given by the equation:

$$P(\text{male})=P(A)*P(B).$$

This analysis is performed automatically by the APL system for each of the samples processed by the mass spectrometer. Based on these probabilities, the APL system decides whether the mass spectrometer output identifies a male or a female. If the probabilities indicate an ambiguous outcome, then the mass spectrometer output is considered inconclusive. In the preferred embodiment, a probability is considered conclusive if it is at least ten times the probability of the alternative outcome. Thus, if P(female) is greater than ten times P(male), then the typing decision is for a female. If P(male)>10*P(female), then the typing decision is for a male.

After the analysis has been performed for a sample subject, the APL system checks for additional mass spectrometer output for analysis. As noted above, the APL system can support mass spectrometer output at the rate of hundreds of output sets per hour. As indicated by the decision box 614 in FIG. 6, if more data is present, an affirmative outcome at box 614, then APL control resumes with receiving the next set of output data at the flow diagram box numbered 304. If there is no more mass spectrometer output data for analysis or if a system operator indicates a halt command, a negative outcome at box 614, then the sample run ends and other operation of the APL continues. For example, operation may return to box 602, where more test run input parameters are received and output analysis is resumed. Other processing may occur, as desired.

Databases

In cases of high-throughput, the APL stores results of all samples in all runs in a database. The sample run history may be selected for viewing through an APL user interface such as illustrated in FIG. 7. The user interface permits review of the database created by one or more sample runs. An example of the user interface to such a database is shown in the screen display of FIG. 8. The database provides a means of obtaining test output, reaction details, sample details, and assay details for each sample under test. For example, shown as output collected in the database are the sample plate number, location of the sample well, sample and plate IDs, name, result of genotype matching, and actual spectrum for each sample.

A database analysis system is also integrated into the APL system (see FIG. 7) and permits a user to (1) create a new run; (2) copy an existing run; (3) edit or view an existing run; (4) change status or add comment; (5) view the history of a run; and (6) create or edit an assay or test. In the preferred embodiment, the database is supported by a database management system from Oracle Corporation.

The processes, systems, and products provided herein have been described above in terms of a presently preferred embodiment. There are, however, many configurations for automated process lines not specifically described herein but that are apparent from the disclosure herein. The disclosure herein is not limited to the particular embodiments described herein, but rather, is understood to have wide applicability with respect to automated process lines generally, particularly in the areas of diagnostics and high throughput screening protocols. All modifications, variations, or equivalent arrangements and implementations that are within the scope of the attached claims should therefore be considered within the scope of the invention.

Since modifications will be apparent to those of skill in this art, it is intended that this invention be limited only by the scope of the appended claims.

What is claimed is:

1. A data analysis system comprising:

a computer having an operating environment that executes a data analysis program for processing test results from a process line having a plurality of processing stations, each of which performs a procedure on a biological sample contained in a reaction vessel, wherein one of the processing stations comprises a mass spectrometer;

a data analysis program for processing the test results by receiving test results from one or more of the processing stations;

removing a residual baseline from the test data from the mass spectrometer for a biological sample;

curve fitting each peak of the biological sample test data to predetermined input parameters;

determining a probability that each peak of the biological sample test data is a valid peak; and making a data typing decision regarding the biological sample in accordance with the determined valid peaks; and a computer interface that receives the test results from the process line and provides the test results to the data analysis program, wherein the data analysis program automatically processes the test results to make a determination regarding the biological sample in the reaction vessel, and continuously performs such processing for biological samples until a stop instruction is received.

2. A data analysis system of claim 1, wherein the reaction vessel comprises a multiple-well plate.

3. A data analysis system of claim 1, wherein the data analysis system displays exemplary test spectra for data types to be determined by the data analysis system, along with a graph of test data picked peaks and a graph of smoothed test spectra data for a biological sample.

4. A data analysis system of claim 1, wherein the data analysis system receives test run input parameters that determine processing until a different set of input parameters are received.

5. A data analysis system of claim 4, wherein the data analysis system displays exemplary test spectra for data types to be determined by the data analysis system, along with a graph of test data picked peaks and a graph of smoothed test spectra data for a biological sample, and the input parameters specify display parameters.

6. A data analysis system of claim 1, wherein the data analysis system removes the residual baseline from the test data by modeling the baseline of the mass spectrometer data with a quadratic equation specified by the input parameters.

7. A data analysis system of claim 6, wherein the input parameters specify a range of data over which the baseline will be modeled.

8. A data analysis system as defined in claim 7, wherein the baseline is modeled over a peak, free region specified by the input parameters.

9. A data analysis system as defined in claim 5, wherein the picked peaks graph represents all peaks in the mass spectrometer output that have a height that exceeds the residual baseline corrected data.

10. A data analysis system as defined in claim 9, wherein the data analysis system validates a peak after comparing a probability density function for the peak free region with a probability density function for a fitted peak if the comparison shows that the respective probability density functions overlap by a predetermined amount.

11. The system of claim 1, wherein the mass spectrometric format is matrix assisted laser desorption time-of-flight analysis (MALDI-TOF).

12. A data analysis system of claim 1, wherein the data typing decision is a genotype.

13. A data analysis system of claim 1, wherein the predetermined input parameters serve as landmarks to identify output shifting.

14. A data analysis system of claim 1, further comprising an operator interface.

* * * * *